United States Patent [19]
Asahina et al.

[11] Patent Number: 5,539,798
[45] Date of Patent: Jul. 23, 1996

[54] X-RAY RADIOGRAPHIC APPARATUS

[75] Inventors: Hiroshi Asahina; Naoki Yamada, both of Nishinasuno-Machi; Hiroshi Nakayama; Masahiro Ozawa, both of Otawara; Toyomitsu Kanebako, Nishinasuno-Machi, all of Japan

[73] Assignee: Kabushiki Kaisha Toshiba, Kawasaki, Japan

[21] Appl. No.: 187,064

[22] Filed: Jan. 27, 1994

[30] Foreign Application Priority Data

Jan. 27, 1993 [JP] Japan ................................. 5-011869

[51] Int. Cl.$^6$ ................................................ H05G 1/64
[52] U.S. Cl. ........................ 378/98.5; 378/63; 378/98.7
[58] Field of Search ............................ 378/98.5, 98.7, 378/63

[56] References Cited

U.S. PATENT DOCUMENTS

| | | | |
|---|---|---|---|
| 4,246,607 | 1/1981 | Vijverberg | 378/98.5 |
| 4,472,826 | 9/1984 | van de Ven | 378/98.5 |
| 4,769,701 | 9/1988 | Sblebitz et al. | 378/41 |
| 4,875,225 | 10/1989 | Hunold | 378/98.5 |
| 4,907,252 | 3/1990 | Aichinger | 378/98.5 |

FOREIGN PATENT DOCUMENTS 59-17590   4/1984   Japan.

Primary Examiner—Craig E. Church
Attorney, Agent, or Firm—Oblon, Spivak, McClelland, Maier & Neustadt

[57] ABSTRACT

An X-ray radiographic apparatus comprises an X-ray tube having an X-ray focal point for radiating X-ray beams toward an object being examined, an X-ray beam limiting device incorporating a limiting member making an aperture for limiting the X-ray beams passing therethrough, the aperture being adjustable in size, and an element for obtaining a surface image of the object through the aperture. The obtained surface image is utilized in various aspects. One aspect is control of the size of the aperture by comprising an element for forming a frame image representing the aperture in accordance with a given size information, an element for displaying the surface image on which the frame image is superposed, a specifying element for being able to specify by hand a size of the frame image by giving the size information to the frame image forming element, and an element for driving the limiting member so that the size of the aperture is brought into a size specified by the aperture displayed on the surface image displaying element. Another aspect concerns positioning using a reference image and automatic exposure control.

49 Claims, 17 Drawing Sheets

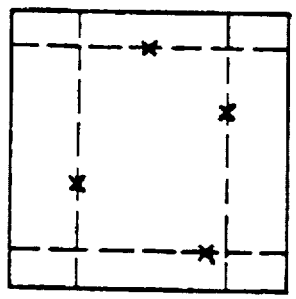 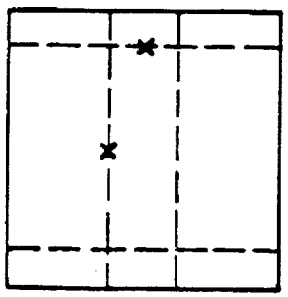 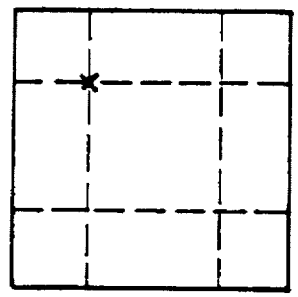
FIG. 5A  FIG. 5B  FIG. 5C
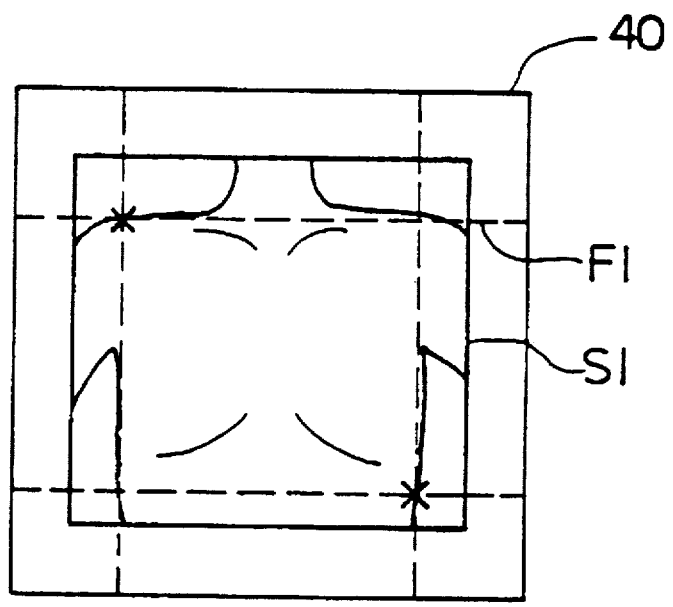
FIG. 6

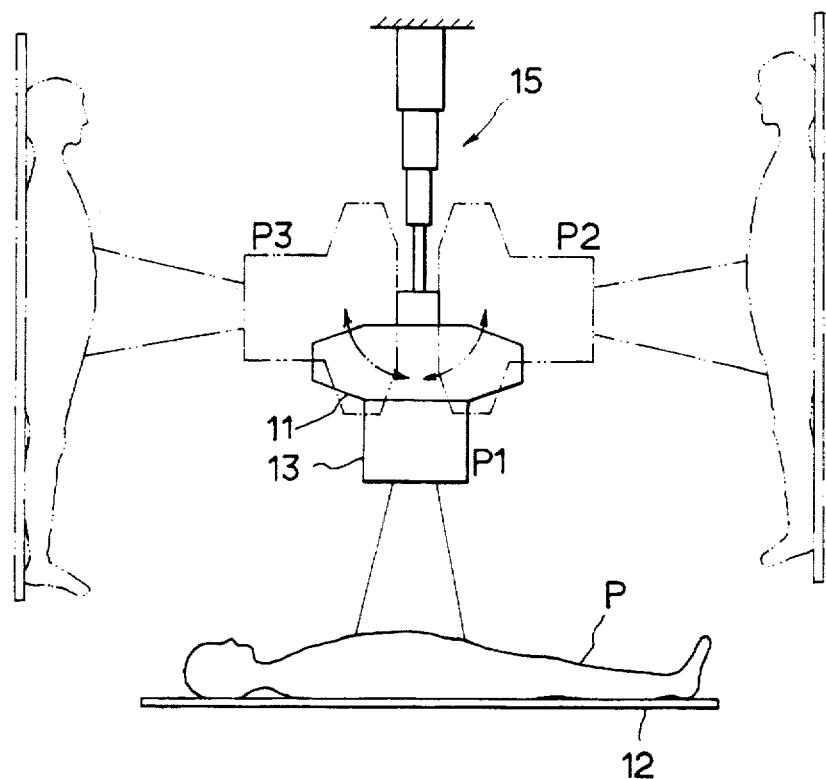
FIG. 22
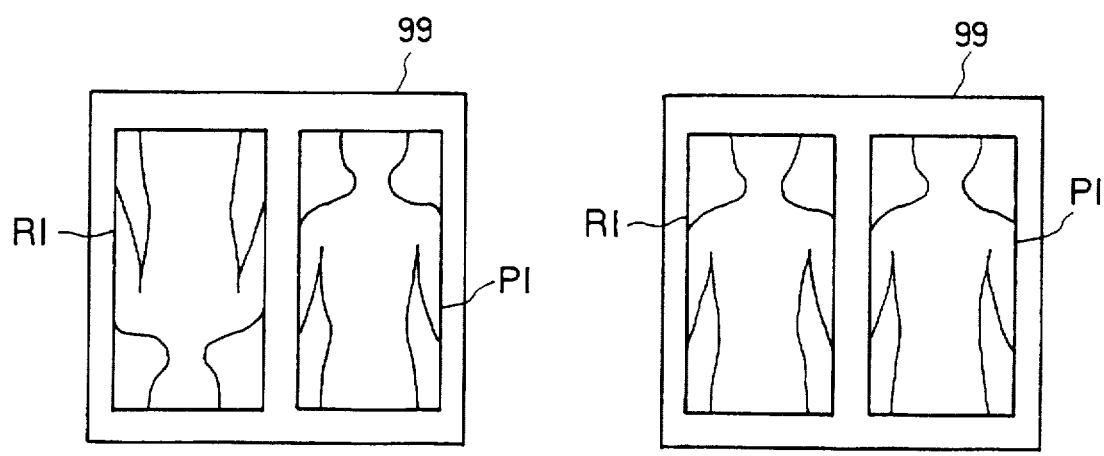
FIG. 23A
FIG. 23B

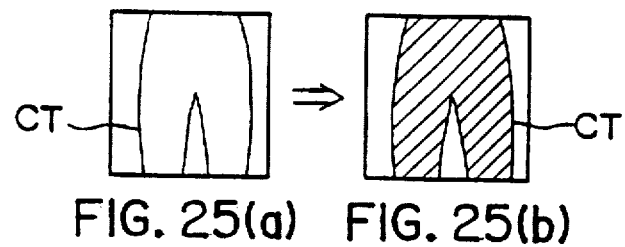
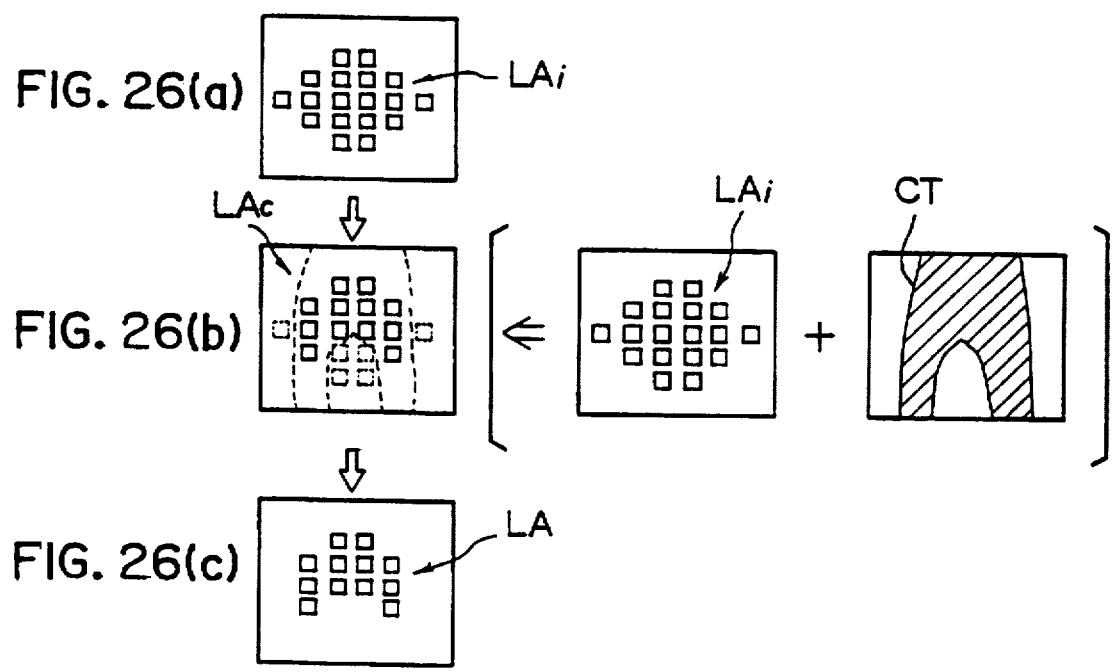
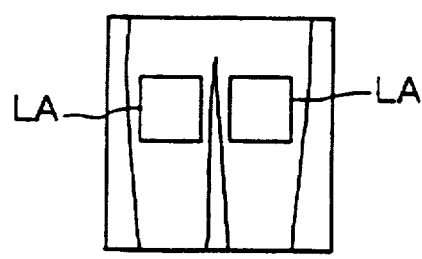

X-RAY RADIOGRAPHIC APPARATUS

BACKGROUND OF THE INVENTION

The present invention relates to an X-ray radiographic apparatus, in particular, to the X-ray radiographic apparatus incorporating an optical camera for obtaining a surface image of an object being imaged, the optical camera being arranged in an X-ray beam limiting device for limiting X-ray beams radiating from an X-ray tube toward the object.

In X-ray radiography, there are two radiographic methods; one is a direct radiographic method by which an X-ray image can be obtained by exposing transmitted X-rays through an object body onto an X-ray film, while the other is an indirect radiographic method by which transmitted X-rays are converted by an image intensifier (I.I.) into visible light rays received by a TV camera to obtain an X-ray image. An X-ray radiographic apparatus employing such methods has been widely used in examinations of digestive tracts and bronchial tubes using contrast medium and other examinations.

An X-ray radiographic apparatus comprises an X-ray tube radiating X-ray beams and an X-ray beam limiting device limiting the X-ray beams from the X-ray tube for avoiding excess X-ray exposure. The X-ray beam limiting device incorporates a set of limiting blades forming an aperture for X-ray beams. Thus, adjusting the size of the aperture permits an X-ray radiation field to be specified into a desired size on the object.

FIG. 1 shows a conventionally used X-ray radiographic apparatus 1 having an X-ray tube 2 and an X-ray beam limiting device 3. In the limiting device 3, a lamp 4 is disposed at a position that is conjugate to an X-ray focal point FP of the X-ray tube 2. As shown in the figure, X-ray beams radiated from the focal point FP of the X-ray tube 2 reaches a patient P lain on a tabletop 5 of a patient couch.

Lighting up the lamp 4 allows its light rays to reflect on a mirror 6 and then to radiate onto the object P, so that a light radiation field from the lamp 4 is coincident with an X-ray radiation field.

Accordingly, prior to X-ray exposure in X-ray examination, the X-ray radiation field is known to an operator by lighting up the lamp 4. Therefore, in normal conditions, the operator has used the light radiation field to adjust the aperture of a limiting member 3a incorporated in the X-ray beam limiting device 3 and to adjust relative positional relation among the X-ray tube 2, the patient P, and X-ray beam receiving devices such as an X-ray film 7 (or cassette or image intensifier).

However, when the above X-ray radiographic apparatus is used, it is required that the radiographic room be rather dark to confirm the light radiation field (i.e., X-ray radiation field) of the lamp. The darker room requires not only much operation time for the above-mentioned various adjustments but skilled operation techniques. These drawbacks are enhanced in mass screening, thereby causing a longer examination time in mass screening.

In case that the head portion of a patient is examined, dazzling light beams fall into the patient's eyes, imposing considerable endurance on the patient.

Further, when considering the longevity of the lamp, it is preferred to avoid lighting up the lamp for a longer period of time at one time. However, a shorter operation time sometimes causes an operator to be inconvenient for obtaining a highly accurate aperture of the X-ray limiting member.

Still further, fluoroscopy using a small quantity of X-ray may be carried out in the above-mentioned indirect radiography employing an image intensifier. In such a case, the aperture of an X-ray limiting device is sometimes adjusted with a fluoroscopy image. This results in an excessive X-ray exposure to a patient.

On the other hand, the above-mentioned drawbacks are also true in stereoradiography that uses an X-ray tube having a pair of X-ray focal points therein.

SUMMARY OF THE INVENTION

Accordingly, it is a primary object of the present invention to provide an X-ray radiographic apparatus that is able to improve maneuverability for specifying a desired X-ray radiation field to shorten an X-ray examination time.

Further, it is another object to provide an X-ray radiographic apparatus that is favorable to mass screening in particular.

Still further, it is another object to provide an X-ray radiographic apparatus by which an operator can readily recognize the position of a portion being diagnosed in a procedure of positioning.

Still further, it is another object to provide an X-ray radiographic apparatus by which an excessive X-ray exposure is avoidable when specifying an X-ray radiation field and radiography conditions.

These and other objects can be achieved according to the present invention, in one aspect by providing an X-ray radiographic apparatus comprising an X-ray tube having an X-ray focal point for radiating X-ray beams toward an object being examined, an X-ray beam limiting device incorporating a limiting member making an aperture for limiting the X-ray beams passing therethrough, the aperture being adjustable in size, an element for obtaining a surface image of the object through the aperture, an element for forming a frame image representing the aperture in accordance with a given size information, and an element for displaying the surface image on which the frame image is superposed.

It is preferred that the X-ray radiographic apparatus further comprises a specifying element for being able to specify by hand a size of the frame image by giving the size information to the frame image forming element. It is also preferred that the X-ray radiographic apparatus further comprises an element for driving the limiting member so that the size of the aperture is brought into a size specified by the aperture displayed on the surface image displaying element.

In another aspect according to the present invention, there is also provided an X-ray radiographic apparatus comprising an X-ray tube having two X-ray focal points for each radiating X-ray beams toward an object being examined, an X-ray beam limiting device incorporating two limiting members each making apertures for limiting the X-ray beams passing therethrough, the apertures being adjustable in size, an element for obtaining surface images of the object through each of the apertures, and an element for displaying each of the surface images.

In another aspect according to the present invention, there is also provided an X-ray radiographic apparatus comprising an X-ray radiographic apparatus comprising an X-ray tube having an X-ray focal point for radiating X-ray beams toward an object being examined, an X-ray beam limiting device incorporating a limiting member making an aperture for limiting the X-ray beams passing therethrough, an element for obtaining a surface image of the object through the aperture, an element for obtaining a reference image for positioning of X-ray radiography, and an element for displaying the surface image and reference image simultaneously.

In another aspect according to the present invention, there is also provided an X-ray radiographic apparatus comprising an X-ray tube having an X-ray focal point for radiating X-ray beams toward an object being examined, an X-ray beam limiting device incorporating a limiting member making an aperture for limiting the X-ray beams passing therethrough, an element for receiving the X-ray beams transmitted through the object, an element for obtaining a surface image of the object through the aperture, an element for extracting a contour image of the object from the surface image, an element for setting a light pickup area image on the extracted contour image; and an element for controlling exposure of the X-ray tube on the basis of an amount of the received X-ray beams on the set light pickup area,

BRIEF DESCRIPTION OF THE DRAWINGS

The accompanying drawings which are incorporated in and constitute a part of this specification, illustrate embodiments of the present invention and, together with the description, serve to explain the principles of the present invention; in which:

FIGS. 5A to 5C each shows examples of methods of specifying a limiting frame image;

FIG. 6 is an example of a limiting frame;

FIG. 22 is a pictorial explanation of rotation of an X-ray tube;

FIG. 23A exemplifies a monitor image explaining a drawback for rotation of an X-ray tube;

FIG. 23B exemplifies a monitor image obtained in the ninth embodiment;

FIG. 25 is an explanation for extracting a contour;

FIG. 26 is an explanation for specifying a light pickup area; and

FIG. 27 is an example of a light pickup area.

DESCRIPTION OF THE PREFERRED EMBODIMENTS

A first embodiment of the present invention will now be described with reference FIGS. 2 and 3.

Figure 1:
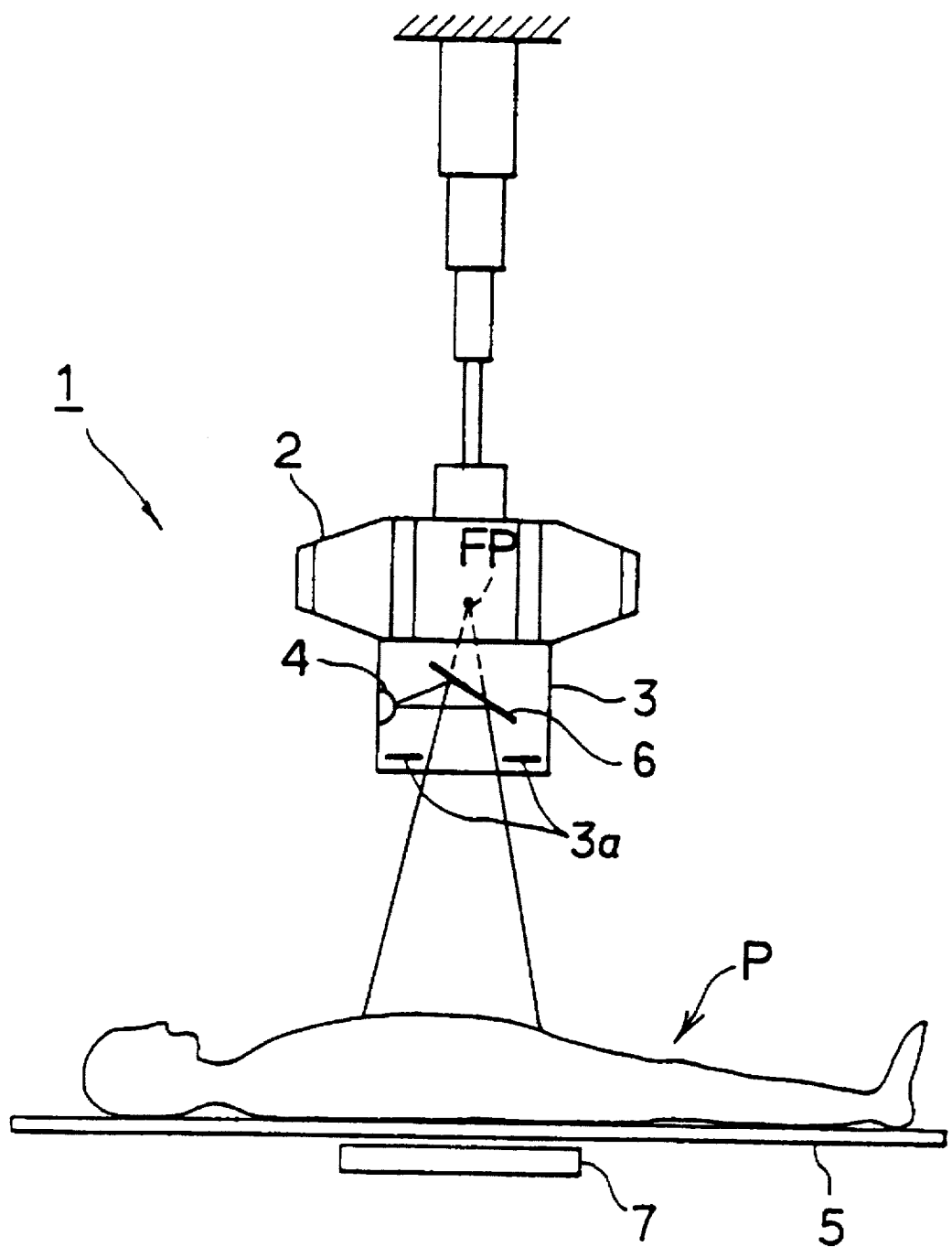
FIG. 1 is a block diagram showing a prior art.
Figure 2:
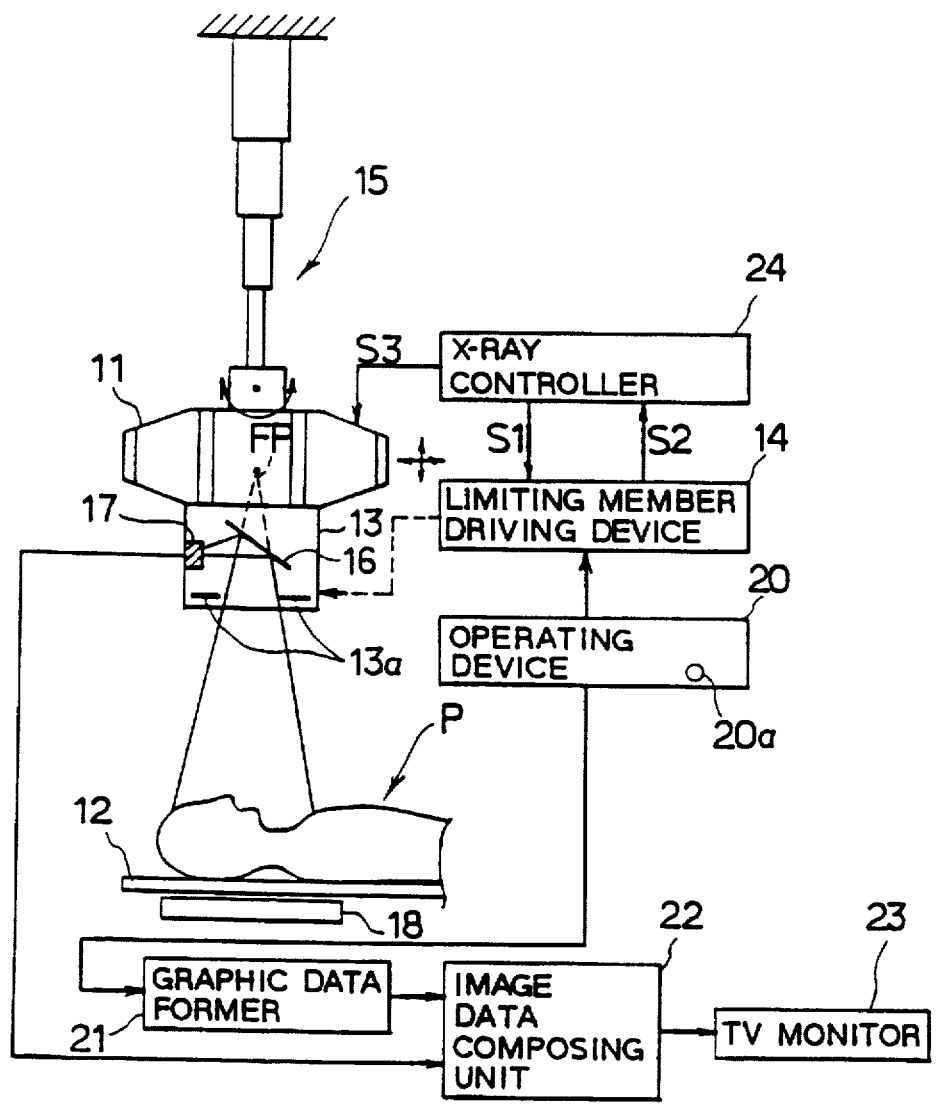
FIG. 2 is a block diagram of an X-ray radiographic apparatus according to a first embodiment of the present invention.
Figure 3:
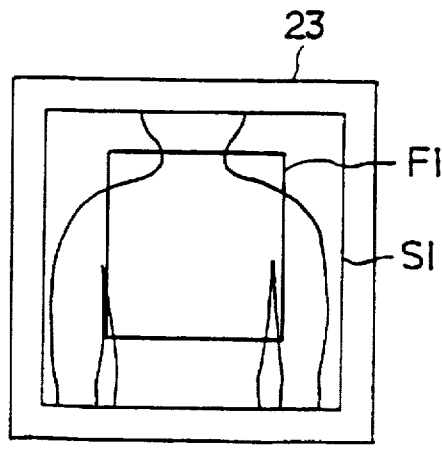
FIG. 3 shows an example of a monitor image of the first embodiment.

FIG. 2 shows a construction of an X-ray radiographic apparatus according to this embodiment. The X-ray radiographic apparatus shown therein comprises an X-ray tube 11 having a single X-ray focal point FP. The X-ray tube 11 radiates X-ray beams from its focal point FP toward a patient P as an object to be examined lain on a tabletop 12 of a patient couch (not shown). At the X-ray radiation side of the X-ray tube 11, an X-ray beam limiting device 13 is attached for limiting X-ray beams radiated from the X-ray tube 11 into a desired size of an X-ray radiation field on the surface of the patient P.

The limiting device 13 incorporates a set of lead-made blades forming a limiting member 13a. The limiting member 13a has a square aperture whose size is adjustable by a limiting member driving device 14 including driving means such as electric motors. Although not shown in the figure, the driving device 14 is partly arranged in the limiting device 13.

The X-ray tube 11 is suspended from, for example, the ceiling by a support device 15 that is constructed to be able to move the tube 11 up and down, move it horizontally and rotate it around its lateral axis, as shown by arrows in the figure. Further, in the X-ray beam limiting device 13, a mirror 16 is disposed on the way of the X-ray beam path, being able to pass radiated X-ray beams therethrough, but being able to reflect light beams thereby.

There is further provided an optical TV camera 17 at an optically conjugate position to the X-ray focal point FP within the limiting device 13. The conjugate position is the same as a position where a conventionally-used lamp has been disposed. In consequence, the TV camera 17 is able to obtain a partial surface image of the patient P through a field depending on a size of the adjustable aperture of the limiting member 13a; in other words, the size of the partial surface image obtained by the TV camera 17 exactly represents the size of an X-ray radiation field determining an X-ray radiographic region.

Below the tabletop 12, there is an X-ray film cassette 18 containing X-ray films, which will receive transmitted X-ray beams through a patient p.

The X-ray radiographic apparatus further comprises, as shown in FIG. 2, an operating device 20, a graphic data former 21, an image data composing unit 22 and a TV monitor 23 as well as an X-ray controller 24.

The operating device 20 is used by hand for adjusting the aperture size of the limiting member 13a of the limiting device 13. This operating device 20 has not only a CPU system including a memory therein but a knob 20a for use by an operator. Operating the knob 20a permits the operating device 20 to provide the graphic data former 21 a signal representing data of a desired aperture size given through the knob 20a. Further, the operating device 20 is capable of temporarily memorizing in its memory a target value of a desired aperture size finally determined by the operator.

In response to a signal representing an aperture size (i.e., the size of gradation field) from the operating device 20, the limiting member driving device 14 is able to adjust its aperture size. This driving device 14 is also communicable with the X-ray controller 24.

The graphic data former 21 is to form in real time graphic data representing a frame of the aperture of the limiting member 13a (hereinafter, referred to as limiting frame), in response to the aperture data supplied from the operating device 20

The image data comprising unit 22 is connected at its two inputs to the TV camera 17 and graphic data former 21 to receive the data of a surface image and graphic data of aperture frame, respectively. The image data composing unit 22 composes, into one frame data, image data through selecting, pixel by pixel, either one data between positionally corresponding two pixels of the frame data of and the surface image data supplied and send the composed image data in real time frame by frame to the TV monitor 23 to show the image data thereon.

On one hand, the X-ray controller 24 is able to communicate with the limiting member driving device 14 and to control the operation of the X-ray tube 11 in accordance with a given procedure.

The overall operation of the present embodiment will now be explained.

When the X-ray radiographic apparatus initiates its operation, the limiting member driving device 14 moves the limiting member 13a of the beam limiting device 13 to a position of a full aperture size as an initial state, thus its aperture is full open. In such a state, a partial surface image of a patient P is taken by the TV camera 17 through the limiting member 13 in full open. The image data thus-obtained is then sent to the image data composing unit 22.

The knob 20a of the operating device 20 is then adjusted by hand with the TV monitor 24 observed, so that a corresponding aperture size signal to an adjusted position of the knob 20a is sent to the graphic data former 21. In this former 21, a graphic data representing a frame specified by the aperture size signal is generated in real time and then supplied to the image data composing unit 22.

Therefore, the surface image data and frame graphic data are synthesized into a one frame data in real time in the composing unit 22. The composed image data are sent to the TV monitor 23 to display them thereon. Thus the TV monitor 23 displays an image shown in FIG. 3, for example, in which a limiting frame image FI represented by a square line is superimposed on a partial surface image SI of the patient P. Since the TV camera 17 is disposed at an optically conjugate position to the X-ray focal point FP, the size of frame image can be regarded as an X-ray radiation field for radiography which will be carried, based on an instruction from the X-ray controller 24.

In this situation, if the operator is unsatisfied with the size of the frame image now displayed on the TV monitor 23, he or she operates the knob 20a to readjust the size of the limiting frame image FI, corresponding to the aperture of the limiting member 13a. Readjusting the knob 20a permits the graphic data former 21 and image data composing unit 22 to display, in real time, an updated image on the TV monitor 23, in which a readjusted limiting frame image FI is superimposed on the partial surface image SI.

Accordingly, such readjustment will be repeated until a desired size of the limiting frame image FI appears on the TV monitor 23. In parallel with such adjustment, positioning of the X-ray tube 11 and patient P will be carried out so that a desired diagnostic portion of the patient P falls within the desired limiting frame image FI.

On having completed the above-mentioned positioning of the X-ray tube and patient and adjustment of the aperture size, a finally determined size of the aperture (i.e., a desired limiting frame image size, or a desired X-ray radiation field) is temporarily stored, as a target aperture size, in the memory of the limiting member driving device 14. In this stage, the actual aperture size of the limiting member 13a has been still fully open.

Then, an X-ray exposure switch (not shown) is pushed to give an instruction of exposure to the X-ray controller 24. In response to the exposure instruction, an aperture specifying signal SI is sent to the limiting member driving device 14, which reads out the target aperture size stores so far and control the actual aperture size of the limiting member 13a into the target value. After completing this actual control of the aperture size, the limiting member driving device 14 send a completion signal S2 back to the X-ray controller 24.

When receiving the completion signal S2, the X-ray controller 24 drives the X-ray tube 11, in the same fashion as conventional one, by giving it an X-ray exposure signal S3, thus causing the X-ray tube 11 to radiate X-ray beams toward the patient through the aperture of the limiting member 13a, whose aperture size has already been set into the target value.

In this way, while the actual aperture size is kept fully open, a desired target aperture size is adjusted and specified with a supposed image of a limiting frame superimposed on a partial surface image of a patient. Then, at the exposure stage of X-ray beams, the actual size is carried into the target value.

As a result, it is possible for an operator to observe the entire surface image FI taken by the TV camera 17 as well as the inside of the X-ray radiation field during the positioning and adjustment of the aperture. This means that, during the positioning and aperture adjustment, an operator can easily observe both of an exposed region and a non-exposed region at the same time and recognize the boundary between them. In consequence, an operator can more easily, efficiently and accurately carry out the positioning among the X-ray tube, patient and X-ray film and the adjustment of the aperture size of the X-ray beam limiting device, thereby offering remarkably improved efficiency of operation in preparation prior to X-ray exposure.

The improved operation will lead to a shortened examination time, which is, in particular, advantageous in mass screening.

Further, the amount of exposed X-ray beams can be kept to a minimum, as the area of an X-ray radiation field can be reduced down to its absolutely necessary region for examination.

In addition, even if the examination room is light, observing the TV monitor permits an operator to carry out the positioning and aperture adjustment as stated above. There is also no need to arrange the TV monitor alone in another dark room.

Further, because a lamp seen in the prior art is not used (i.e. lighting-up time is not concerned), there is no limitation in terms of times of positioning and aperture adjustment. This allows more precise positioning and aperture adjustment.

Still further, because light beams are not used, a patient does not receive dazzling light, the patient is relieved of this burden.

A second embodiment will now be explained with reference to FIGS. 4 to 6.

In this embodiment, the same reference numerals will be used to the same components as the first embodiment to simplify explanation. This simplified explanation manner will also be applied to all of the embodiments following after the second embodiment.

Figure 4:
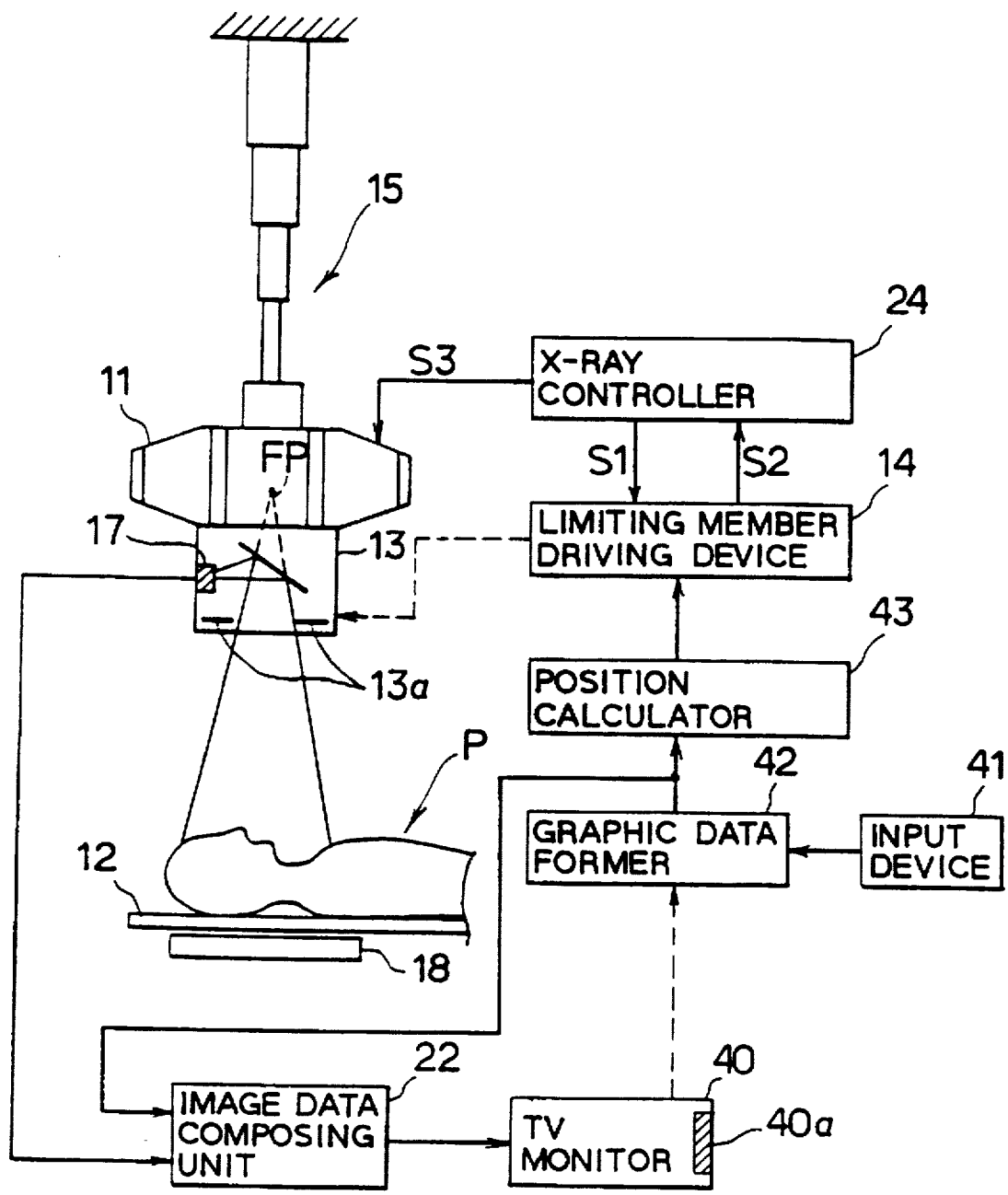
FIG. 4 is a block diagram of an X-ray radiographic apparatus according to a second embodiment of the present invention.

The X-ray radiographic apparatus shown in FIG. 4 comprises a monitor 40 having a touch panel 40a therein, an input device 41 such as a key board, a graphic data former 42, and a position calculator 43, instead of the operating device 20 and graphic data former 21 described before.

An operator is to select one arbitrary method of specifying an aperture limiting frame among several methods prepared beforehand, using the input device 41. In the present embodiment, there are provided three methods: the first method of specifying separately the positions of four segments composing a square limiting frame (refer to FIG. 5A), the second method of specifying the positions of arbitrary adjacent two segments of a square limiting frame (refer to FIG. 5B), and a third method of specifying the position of an arbitrary one corner point of a square limiting frame (refer to FIG. 5C). In case that the first method is selected from the input device 41, an operator is to specify four points by hand on the touch panel 40a, as shown in FIG. 5A. In case of the second method, an operator is to specify two points, as shown in FIG. 5B. In case of the third method, an operator is to specify one point, as shown in FIG. 5C. The touch panel 40A of the monitor 40 functions as a coordinate input means.

The graphic data former 42 receives a signal representing the specifying method of an aperture limiting frame from the input device 41 and a positional signal from the touch panel 40a. The graphic data former 42 forms and generates graphic data of an limiting aperture frame according to the received signals. When the second specifying method has been selected, the remaining segments, which are face-to-face to the two adjacent segments manually given, is automatically specified at symmetrical positions to the segments according to the manually-specified points. Further, when the third specifying method has been selected, the remaining three corner points are automatically determined at the symmetrical positions to the manually specified corner point. The graphic data thus-formed are sent to both of the position calculator 43 and the image data composing unit 22.

The position calculator 43 calculates the positions blades of the limiting member 13a correspondingly to the graphic data representing an aperture limiting frame specified by hand. The newest calculated position data is stored as its target value in a memory of the calculator 43.

Accordingly, in the same manner as the first embodiment, the limiting member 13a is fully opened at first by the limiting member driving device 14. The TV camera 17 photographs a partial surface portion of a patient P and its surface image SI is displayed on the monitor 41, as shown in FIG. 6.

Then, an operator selects one of the specifying methods of the limiting frame through the input device 41 and, according to the selected method, gives positional information to the touch panel 40a. In consequence, graphic data of a desired limiting frame are formed in the graphic data former 42, the formed graphic data of the limiting frame being sent via the composing unit 22 to the monitor 40. As a result, the Limiting frame image FI is displayed superimposedly on the surface image SI, as represented in FIG. 6, which exemplify a case of the third specifying method.

The size of the limiting frame displayed on the monitor 41 can be changed in real time in response to specification on the touch panel 40a. Therefore, the operator can place a limiting frame image FI of an arbitrary size on the screen of the monitor 41.

Since the area of a limiting frame image FI shows an X-ray radiation field, positioning of the X-ray tube 11 and patient P is performed in such a manner that a desired diagnostic region is put within a finally-specified limiting frame image FI. At this time, the position data of the blades of the limiting member 13a, which corresponds to the finally-specified limiting frame, has been calculated and stored as a target value in the position calculator 43. The procedure of the aperture adjustment and positioning can be repeated, if required, and their performance orders can be opposite.

Further, in response to a start of X-ray exposure, an aperture specifying signal S1 is sent from the X-ray controller 24 to the limiting member driving device 14, thereby all of the blades of the limiting member 13a is adjusted to its desired position providing a desired aperture size, according to the read-out target value from the position calculator 43. On a completion signal S2 being returned to the X-ray controller 24, X-ray exposure begins by sending an X-ray exposure signal S3 to the X-ray tube 11, as explained in the first embodiment.

As apparent from the above, the second embodiment uses the touch panel to directly specify a region corresponding to a desired X-ray radiation field on a monitor. The size of the region can be changed directly on a monitor. Further, according to an operator's will, the most convenient method of specifying a limiting frame image on a monitor may be selected.

Therefore, the second embodiment offer not only the equivalent advantages to the first embodiment but remarkably improved operation for specifying the size of an aperture.

In this embodiment, although a square aperture has been explained, if an aperture is circular, there can be provided another variations; for example, three point data to pass a circle are given on a monitor or a combined data of a central point and a radius for determining a circle is given on a monitor.

By the way, although the above embodiments have been applied to the X-ray radiographic apparatus having an X-ray tube of one focal point, the present invention is also applicable to stereoradiography using an X-ray tube of two X-ray focal points. Such embodiments will be followed.

A third embodiment of the present invention will now be described with reference to FIGS. 7 and 8.

Figure 7:
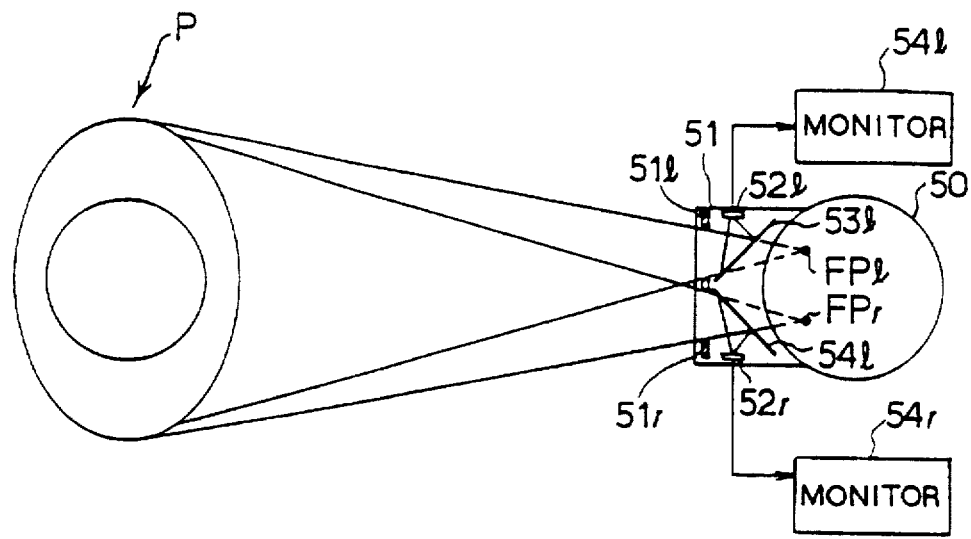
FIG. 7 is a block diagram of an X-ray radiographic apparatus according to a third embodiment of the present invention.
Figure 8:
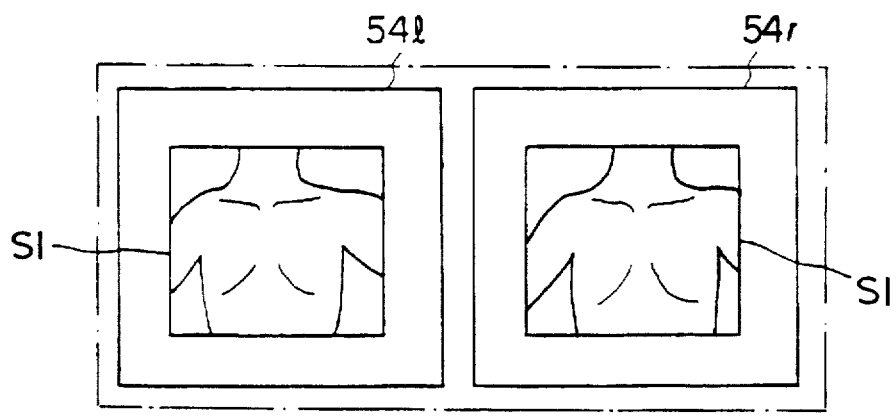
FIG. 8 exemplify monitor images in the third embodiment.

An X-ray radiographic apparatus shown in FIG. 7 comprises an X-ray tube 50 having two focal points FPl and FPr each radiating X-ray beams toward a patient P and an X-ray beam limiting device 51 incorporating a pair of limiting member 51l and 51r limiting the X-ray beams radiated from the two X-ray focal points FPl and FPr. Each of the limiting members 51l and 51r forms an aperture adjustable. At optically conjugate positions to the X-ray focal points FPl and FPr in the X-ray limiting device 51, there are two TV cameras 52l and 52r for each photographing partial surface images of the patient P through the apertures made by the limiting member 51l and 51r. Mirrors 53l and 53r are each disposed on the way of the X-ray beam paths to penetrate the X-ray beams and reflect light beams from the patient P to the TV cameras 52l and 52r through the apertures of the limiting members 52l and 51r, respectively. The TV cameras 52l and 52r are each connected to monitors 54l and 54r placed in a console, for instance.

In this embodiment, light beams reflected on the patient P travel via the apertures of the limiting members 51l and 51r to the mirrors 53l and 53r, respectively. The light beams reflect at the mirrors 53l and 53r and are admitted to the TV cameras 52l and 52r, respectively. Thus, the regions of partial images displayed by the monitors 54l and 54r equal to X-ray radiation fields in such a case that X-ray beams are radiated from the focal points FPl and FPr.

Therefore, while observing surface images on the screen of the monitors 54l and 54r (refer to FIG. 8), an operator not only adjusts the apertures of limiting member 52l and 51r but carry out positioning of the X-ray tube 50 and patient P. After such preparation, X-ray radiography will be carried out.

In this way, the present embodiment employs two TV camera 52l and 52r for photographing partial images each exactly corresponding to X-ray radiation fields. This simplifies the aperture adjustment of the limiting members and the positioning of the X-ray tube and patient for stereoradiography.

Furthermore, in a conventionally used stereoradiography, it was required to light up two lamps alternately in order to distinguish the two X-ray radiation fields from each other on the body surface of a patient. In contrast, the stereo-type X-ray radiographic apparatus according to the present embodiment provides at the same time the two surface images corresponding to the radiation fields, thus enabling simpler operation and stereoradiography to be completed in a shorter examination time.

Figure 9:
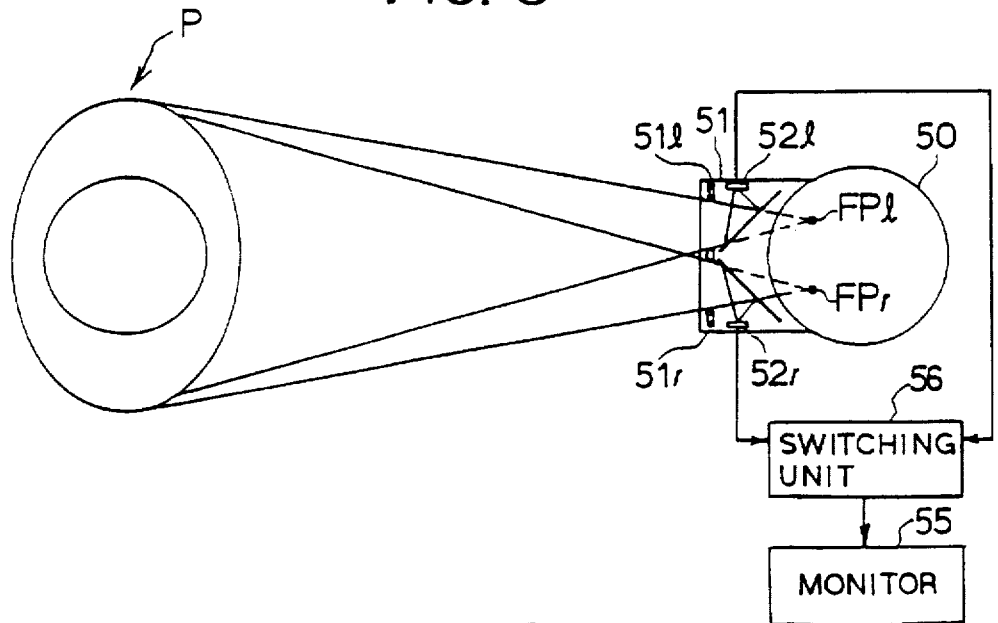
FIG. 9 is a block diagram of an X-ray radiographic apparatus according to a variation of the third embodiment of the present invention.

A variation for the above third embodiment is shown in FIG. 9. In stead of the two monitors, there are only one monitor 55 and a switching unit 56, as shown therein. The switching unit 56 is arranged between the monitor 55 and the TV cameras 52l and 52r and switches the connections therebetween. This construction is able to reduce the monitor in number.

A fourth embodiment of the present invention will now be described with reference to FIGS. 10A through 10C to 11.

Figure 10A:
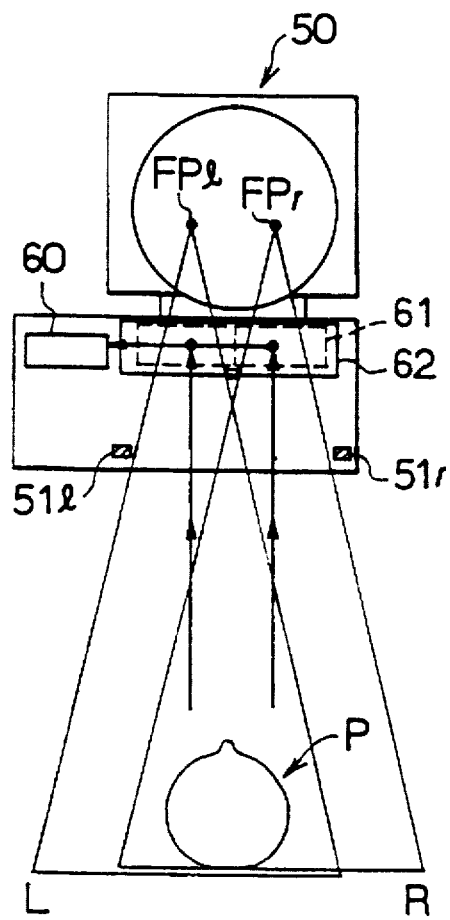
FIG. 10A is a front view of an X-ray radiographic apparatus according to a fourth embodiment of the present invention.
Figure 10B:
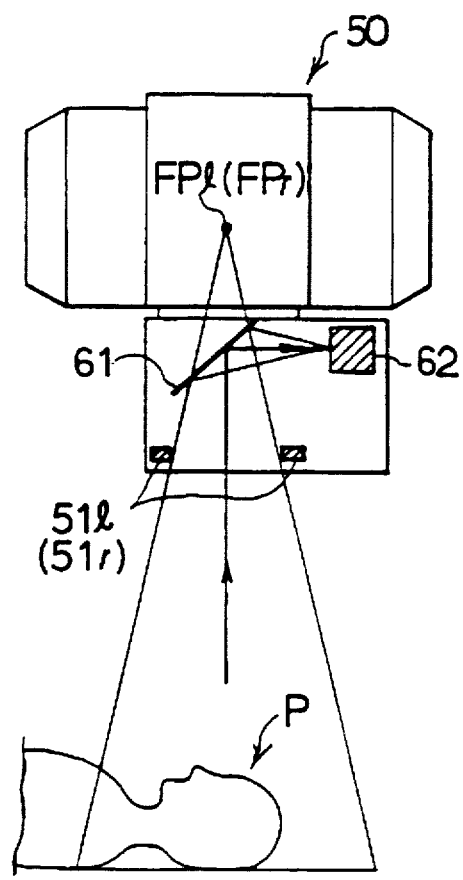
FIG. 10B is a side view of the apparatus shown in FIG. 10A.
Figure 10C:
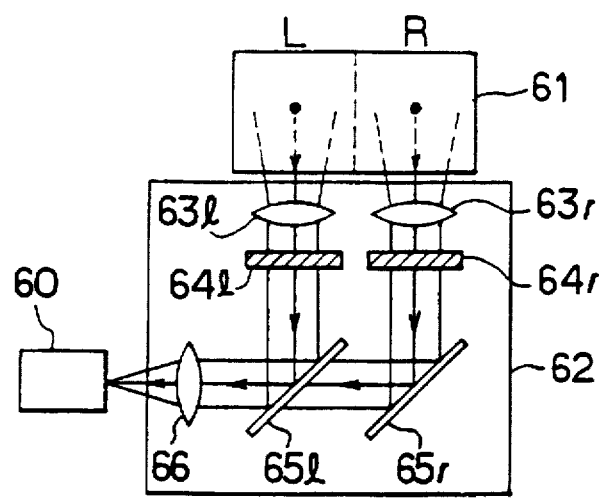
FIG. 10C is a plan view of the apparatus shown in FIG. 10A.

An X-ray stereoradiographic apparatus of the fourth embodiment is shown in FIGS. 10A to 10C, in which FIG. 10A is the frontal view, FIG. 10B is the side view seen from the left side of a patient P, and FIG. 10C is the plan view.

In the X-ray stereoradiographic apparatus, there are only one TV camera 60 photographing a surface image of a patient P and optical systems 61 and 62 guiding, to the TV camera 60, light beams of the right-side surface image (hereinafter, referred to as R-image) and the left-side surface image (hereinafter, referred to as L-image) of the patient P.

One optical system 61 is formed by mirrors, whereas the other optical system 62 incorporates a pair of mirrors 63l and 63r, a pair of shutters 64l and 64r, another pair of a half mirror 65l and a mirror 65r, and a lens 66. The shutters 64l and 64r are made of liquid crystal and are optically opened and closed when applying an electric voltage having a certain level is not applied (OFF) and applied (ON).

The shutters 64l and 64r are operated by drivers later-described in a manner that the R-image and L-image are alternately exchanged. In the optical system 62, the R- and L-images, which are reflected from the optical system 61, are each transmitted to the shutters 64l and 64r. The resultant L- and R-images from the shutters 64l and 64r are reflected by the half mirror 65l and the mirror 65r for a direction of a light axis of the TV camera 60. The reflected L- and R-images are projected to the incident plane of the TV camera 60 by the lens 66.

Figure 11:
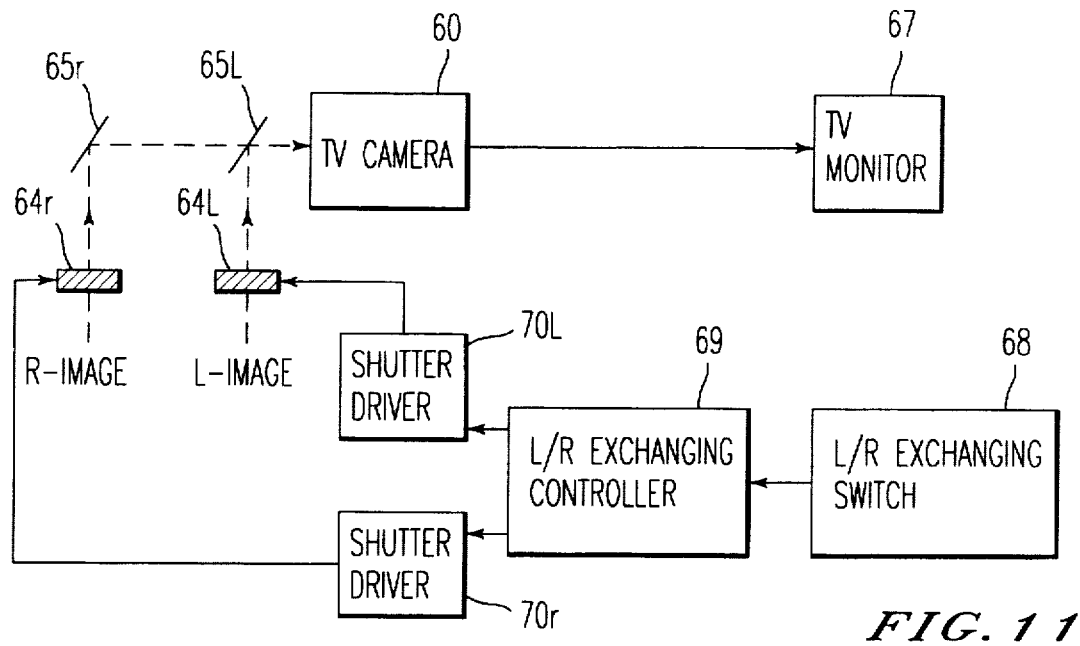
FIG. 11 represents a detailed block diagram for exchanging R- and L-images.

As shown in FIG. 11, in addition to a TV monitor 67 for displaying the L- and R-images photographed by the TV camera 60, there are provided an L/R exchanging switch 68, an L/R exchanging controller 69, and shutter drivers 70l and 70r. The L/R exchanging switch 68 is used by hand for exchanging the open and close of the shutters 64l and 64r. The L/R exchanging controller 69 works in response to signals from the L/R exchanging switch 68. The shutter drivers 70l and 70r are each connected to the shutters 64l and 64r and drive them into an open state (OFF) or a close state (ON) in response to control signals from the L/R exchanging controller 69.

The overall operation will be explained. At first, an operator brings the L/R exchanging switch 68 into a switched state instructing the display of the R-image, for example. In response to the switching, one shutter 64l is closed and the other shutter 64r is opened by the work of the L/R exchanging controller 69 and shutter drivers 70l and 70r.

In this state, as understood from FIG. 10C, the L-image is shut off by the shutter 64l, whereas the R-image, which is reflected by the optical system (mirrors), is transmitted, via the 63r, shutter 64r, mirror 65r, and lens 66, to the TV camera 60.

Hence, only the R-image is displayed on the monitor 67. Observing the displayed R-image, the operator is to perform the adjustment of one limiting member 51r and the positioning between the X-ray tube 50 and patient P.

Next, the operator brings the L/R exchanging switch 68 into another switched state instructing the display of the L-image. In response to the switching, one shutter 64l is opened and the other shutter 64r is closed by the L/R exchanging controller 69 and shutter drivers 70l and 70r.

In this state, as easily understood from FIG. 10C, the R-image is shut off by the shutter 64r. But, the L-image, which is reflected by the optical system 61 (mirrors), is transmitted, via the 63l, shutter 64l, mirror 65l, and lens 66, to the TV camera 60.

Consequently, only the L-image is displayed this time on the monitor 67. Observing the L-image thus-displayed, the operator is to perform the adjustment of the other limiting member 51*l* and the positioning between the X-ray tube 50 and patient P.

If required, exchanges between the L- and R-images are repeated some times in the same manner as the above, and at each time, the aperture adjustment and the positioning on the tabletop may be carried out.

According to this embodiment, the TV camera for photographing is reduced to one in number, because the L- and R-images are guided through optical systems to the TV camera and the shutters are arranged in their optical paths to exchange the L- and R-images alternately. It is possible for one monitor to display the L- and R-images alternately, in response to manual instruction from the L/R exchanging switch. This eliminates the necessity to use two TV cameras and two monitors for stereoradiography. This simplified construction, therefore, is suitable for stereoradiography and enables accurate and quick operation for aperture adjustment and positioning.

A fifth embodiment of the present invention will now be explained according to FIGS. 12 and 13. The fifth embodiment is deformed from the fourth embodiment.

Figure 12:
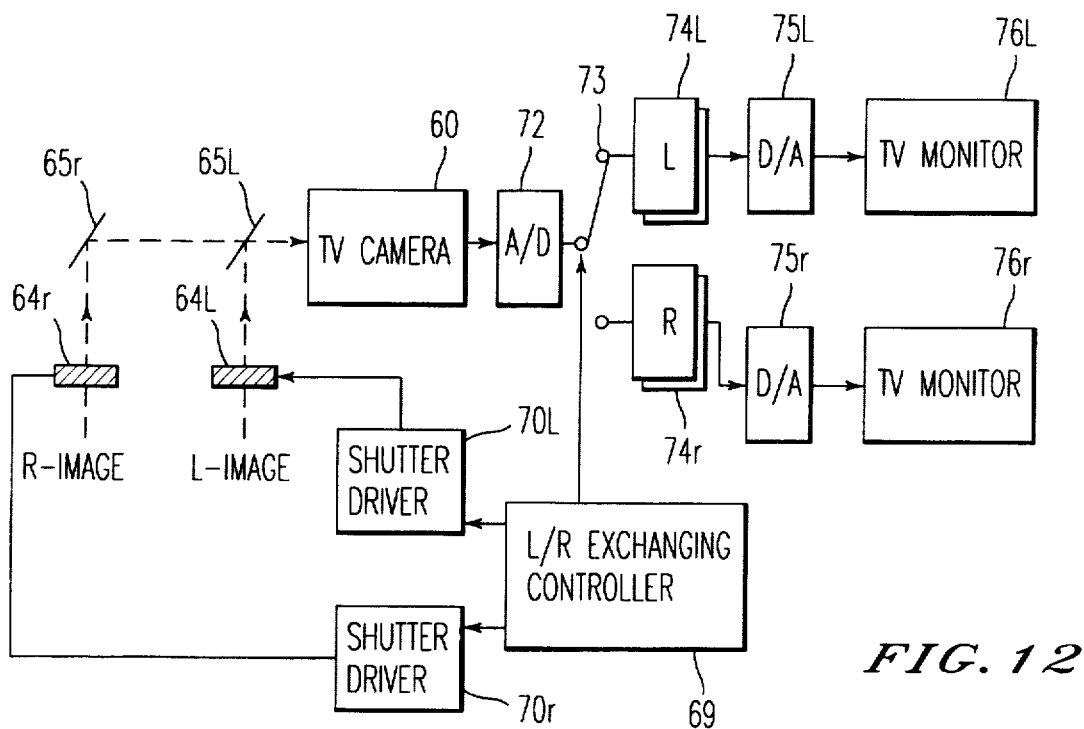
FIG. 12 is a block diagram partly showing an X-ray radiographic apparatus of a fifth embodiment according to the present invention.

An X-ray stereoradiographic apparatus partly shown in FIG. 12 comprises an A/D converter 72 for converting image signals of the L- or R-image from the TV camera 60 into digital quantity. The output of the A/D converter 72 is coupled, through an electric switch 73, with both an image memory 74*l* for the L-.Image and an image memory 74*r* for the R-image. The electric switch 73 switches to either one side of the image memory 74*l* or image memory 74*r*, in response to switching control signal from the L/R exchanging controller 69. Thus, according to contents of the switching control signal, the output image signals of the A/D converter 72 are stored in either one of the image memory 74*l* or 74*r*.

Each of the image memories 74*l* and 74*r* has a double buffer structure to divide the entire memory field into two; one memory field is for writing and the other is for reading. Therefore, for each of the two image memories 74*l* and 74*r*, alternate writing and reading to the divided two memory fields permits simultaneous operation of writing and reading.

The reading outputs of the image memories 74*l* and 74*r* are connected, via D/A converters 75*l* and 75*r*, with an L-side TV monitor 76*l* and R-side TV monitor 76*r*. In consequence, image data written in the image memories 74*l* and 74*r* one frame before can be read out to be displayed on the L- and R-side TV monitors 76*l* and 76*r*.

Furthermore, the L/R exchanging controller 69, not connected to such manually-operated L/R exchanging switch described before, will provide the electric switch 73 a switching control signal instructing the writing of image data into the image memory 74*l* or 74*r*, in response to instructions to the shutter drivers 70*l* and 70*r*. As a result, when one shutter 64*l* is optically shut off, the image data from the TV camera 60 are written into the R-side image memory 74*r* through the electric switch 73; on one hand, when the other shutter 64*r* is optically shut off, the image data are written into the L-side image memory 74*l*.

Figure 13:
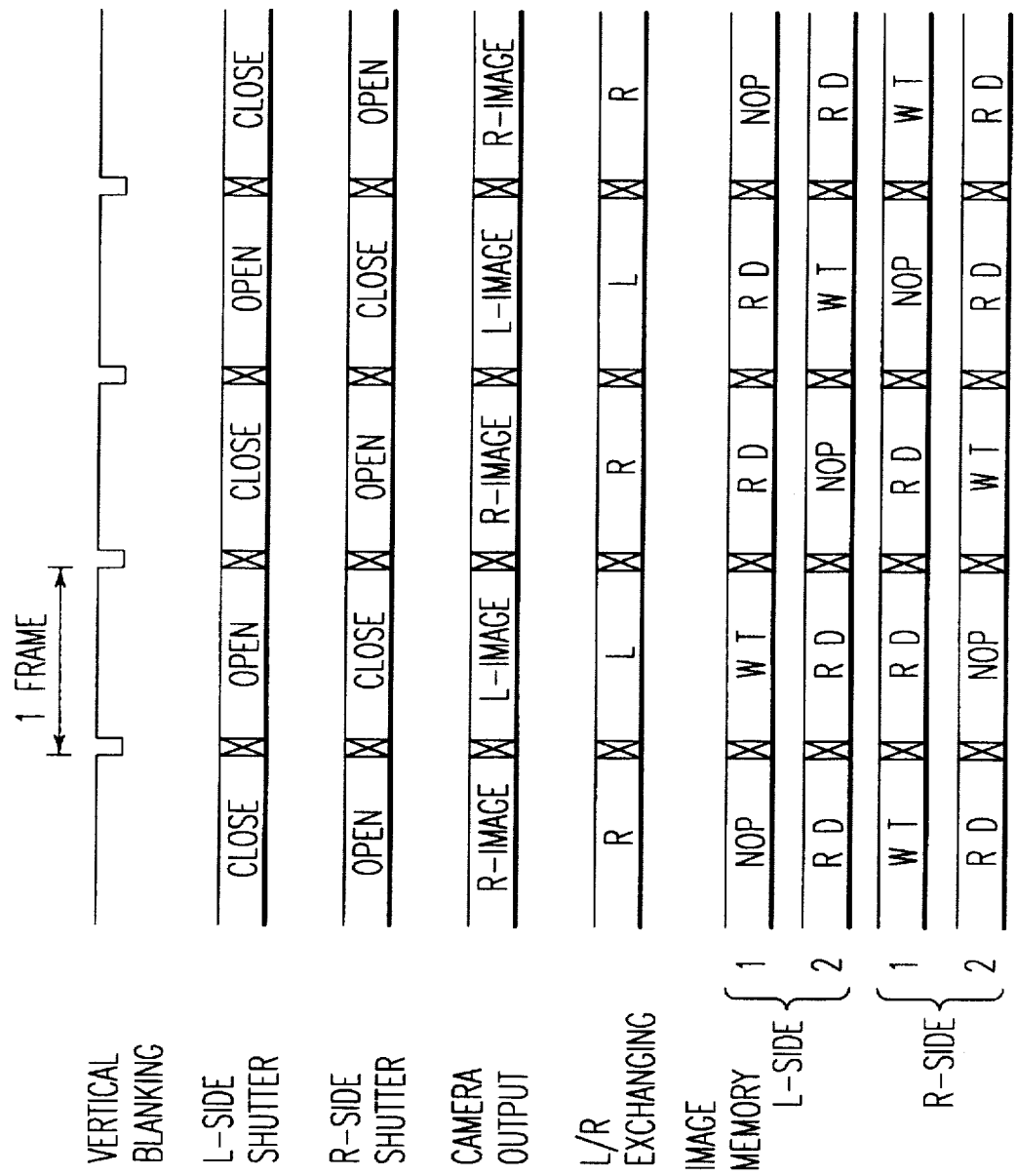
FIG. 13 is a timing chart explaining operation of the fifth embodiment.

In such construction, as shown in FIG. 13, the shutters 64*l* and 64*r* are exchanged to optically open and close every one frame of imaging. For instance, closing the L-side shutter 64*l* and opening the R-side shutter 64*r* allows the R-image to be output from the TV camera 60 to be converted digital quantity.

Further, the writing mode into the image memory 74*l* or 74*r* is turned to the R-side by the L/R exchanging controller 69, thus R-image digital data being written into the R-side image memory 74*r* (R-1 "writing (WT)").

During a period of this writing, image data of both the image memories 74*l* and 74*r*, have been written and stored in two periods of time of the last frame and the frame before last, are read out to convert analog quantity, thus being displayed on the L-side monitor 76*l* and R-side monitor 76*r*, respectively (R-2 "reading (RD)", L-2 "reading").

At the next frame, the R-side shutter 64*r* is closed and L-side shutter 64*l* is opened, the L-image are output from the TV camera 60 to be converted into digital quantity.

Further, the writing mode is exchanged into L-side by the L/R exchanging controller 69 this time, and the digital L-image data are written into the L-side image memory 74*l* (L-1 "writing").

During this writing, image data of both the image memories 41 and 74*r*, have been written and stored in two periods of time of the last frame and the frame before last, are read out to convert analog quantity, thus being displayed on the L-side monitor 76*l* and R-side monitor 76*r*, respectively (R-1 "reading", L-2 "reading").

Repeating the above procedure allows both the two image memories, having a double buffer structure, to a repetitive cycle of "writing, reading, reading, NOP(no operation)" at its order, respectively. In addition, their repetitive cycles are different by two frames between the two divided memory fields of each of the memories 74*l* and 74*r*.

In this way, in the present invention, only one TV camera is used alternately to take the R-image and L-image, and the taken R-and L-images are stored to be displayed at one or two frames later all the time. Though the TV camera is only one, it is therefore possible to provide the human eye almost real time L- and R-images simultaneously. As a result, the whole construction is simple, but the adjustment of the aperture and positioning of the stereo-type X-ray tube and patient can be readily carried out.

A sixth embodiment of the present invention will now be explained using FIGS. 14 and 15, FIG. 14 corresponding to FIG. 12 where the two image memories of the double buffer structure are used and connected to the two separate monitors. In contrast, an X-ray stereoradiographic apparatus partly shown in FIG. 14 incorporates an image memory controller 80 and a single image memory 81 at the output side of the A/D converter 72. The image memory 81, which is controlled by the image memory controller 80, has the double buffer structure that has been explained, but its entire memory field are divided into two fields for L-image side and R-image side, respectively. The output of the image memory 81 is coupled through a D/A converter 82 with a single TV monitor 83.

Figure 14:
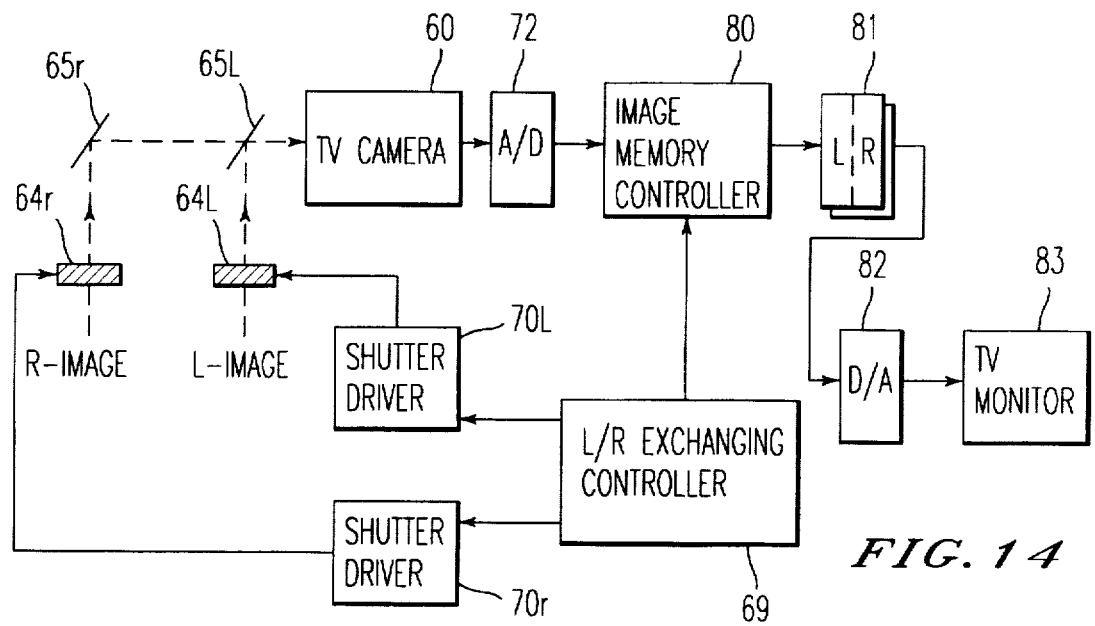
FIG. 14 is a block diagram partly showing an X-ray radiographic apparatus of a sixth embodiment according to the present invention.
Figure 15:
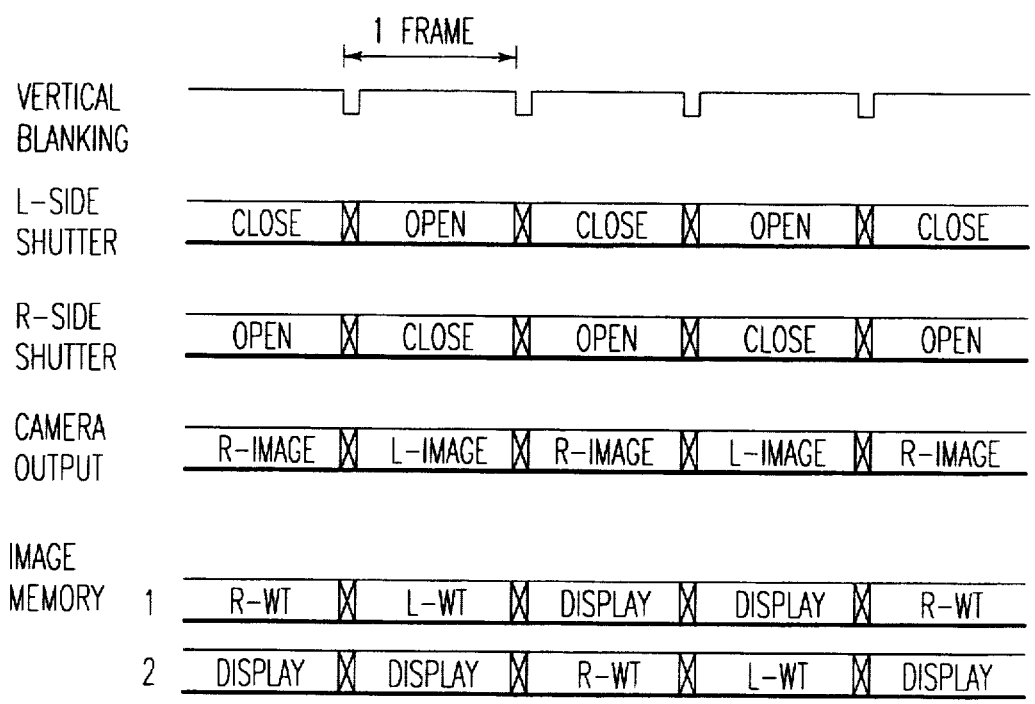
FIG. 15 is a timing chart explaining operation of the sixth embodiment.

Each of the circuits shown in FIG. 14 operates based on a timing chart in FIG. 15, in which the two memory fields of the image memory 81 each repeat a cycle of "R-writing, L-writing, reading, and reading" and other operation is similar to FIG. 13. As a result, the L- and R-images are simultaneously and in parallel displayed on the monitor 83 by means of a multi-window manner.

This one-TV-camera and one-monitor system also provides a simplified construction of the apparatus and almost real time and simultaneous L- and R-images for the human eye, with the result that the apparatus construction is simplified and aperture adjustment and positioning can easily and accurately be carried out.

Although the above embodiments have been explained by adopting a direct radiographic method using X-ray films, but it is possible for the embodiments to adopt an indirect radiographic method using an image intensifier. In case of the indirect radiographic method, a fluoroscopy technique have been utilized for positioning of an X-ray tube and a patient and adjustment of an X-ray beam limiting device. However, applying the present invention to an X-ray radiographic apparatus of the indirect method enables efficient operation and shortened examination times, as explained before, and the least X-ray exposure amount.

A seventh embodiment will now be explained with reference to FIGS. 16 and 17A through 17C. This embodiment is related to the indirect radiography method having an image intensifier and to a positioning technique of a patient on the basis of a photographed image from a TV camera.

Figure 16:
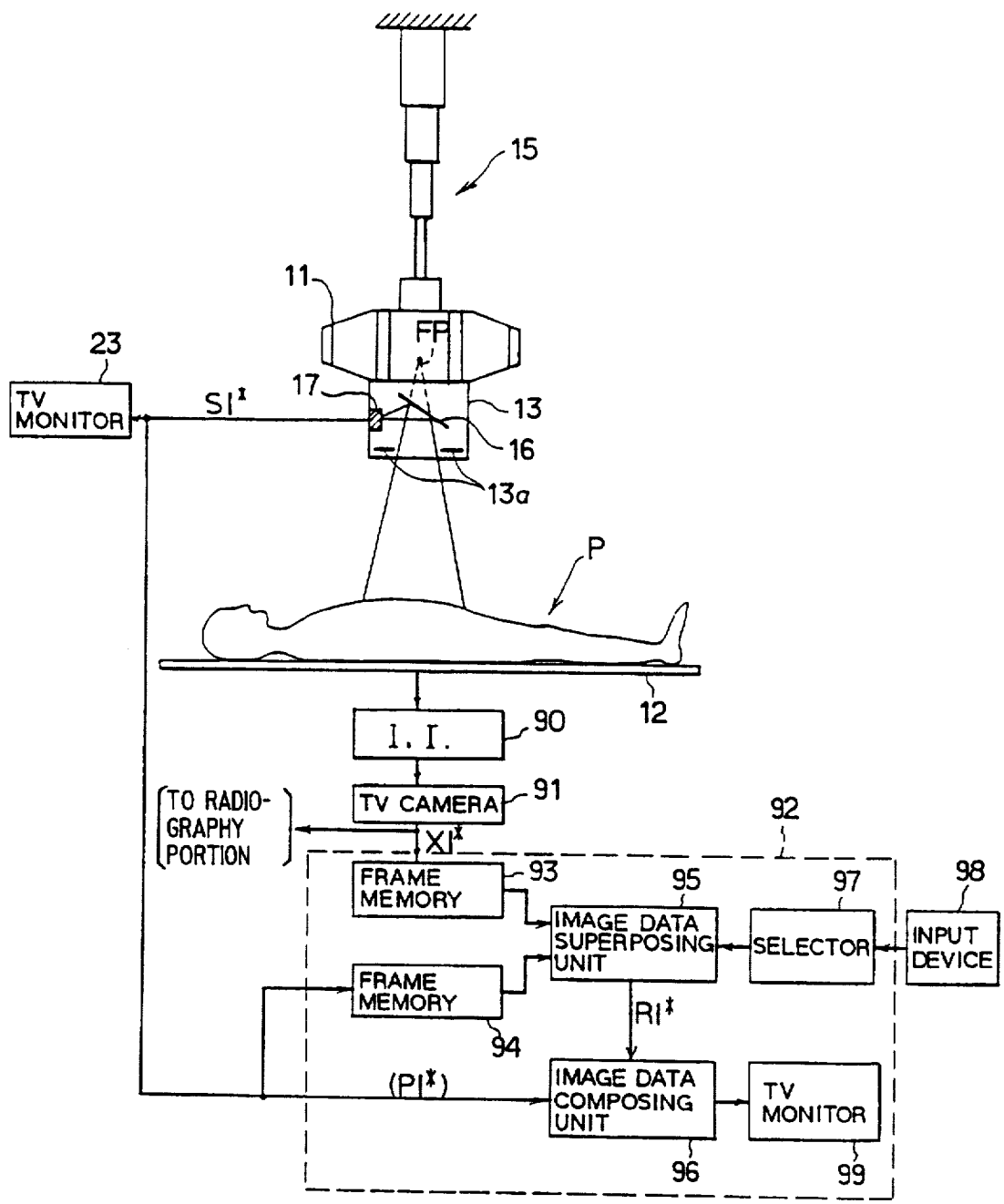
FIG. 16 is a block diagram of an X-ray radiographic apparatus of a seventh embodiment according to the present invention.

An X-ray radiographic apparatus, using a single X-ray focal point, is shown in FIG. 16. In the apparatus, there is provided an X-ray tube 11 having a single X-ray focal point FP. Within the X-ray beam limiting device 13, the TV camera 17 is arranged to an optically conjugate position to the focal point FP. The output of the TV camera 17 is coupled with the TV monitor 23 to directly display a surface image SI of a patient by means of receiving surface image signal SI* taken by the TV camera 17. The surface image SI (refer to FIG. 3, for instance) includes an area corresponding to an X-ray radiation field. As a result, an operator can adjust the aperture of the limiting member 13a in the similar manner described in FIG. 7 or 9.

In the apparatus of the present embodiment, there is further provided an image intensifier 90 for receiving transmitted X-ray beams through the patient P from the X-ray tube 11 and for converting them to corresponding light rays. There are further provided another TV camera 91 for receiving the light rays from the image intensifier 90 and a positioning portion 92 for displaying a positioning image and reference image for positioning. The TV camera 91 converts the received light rays into corresponding electric image signals XI* and outputs them into the positioning portion 92.

The positioning portion 92 comprises a first and second frame memories 93 and 94, in which one memory 93 is connected, at its writing side, to the output of the TV camera 91, whereas the other memory 94 is connected, at its writing side, to the output of the TV camera 17 of the limiting device 13. Hence, the signals XI* of the X-ray image are stored in the first frame memory 93, while the signals S I* of the surface image are stored in the second frame memory 94. The first and second frame memories 93 and 94 are capable of storing a plurality of past frame data, respectively.

The positioning portion 92 further has an image data superposing unit 95 and an image data composing unit 96. The image data superposing unit 95 will read image data from both the frame memories 94 and 95, in addition to selection control signal from a selector 97, forming a part of the positioning portion 92, which receives a signal from an input device 98. The input device 98 is used by an operator for selecting a photographed time of a reference image and combination of images included in a reference image, which will be displayed for positioning of a patient. In response to the signal from the input device 98, the selector 97 sends the corresponding selection control signal to the image data superposing unit 95.

When receiving the selection control signal (specifying a photographed time and combination of images) from the selector 97, the image data superposing unit 95 reads out from both the frame memories 93 and 94 and superpose them, according to contents of the selection control signal.

Figure 17A:
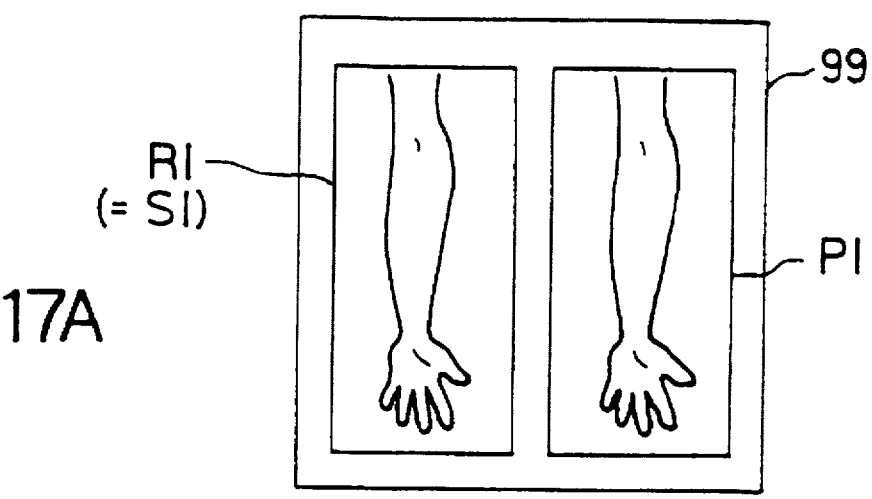
FIGS. 17A to 17C exemplify each monitor screens showing combined images of a reference image and a positioning image.
Figure 17B:
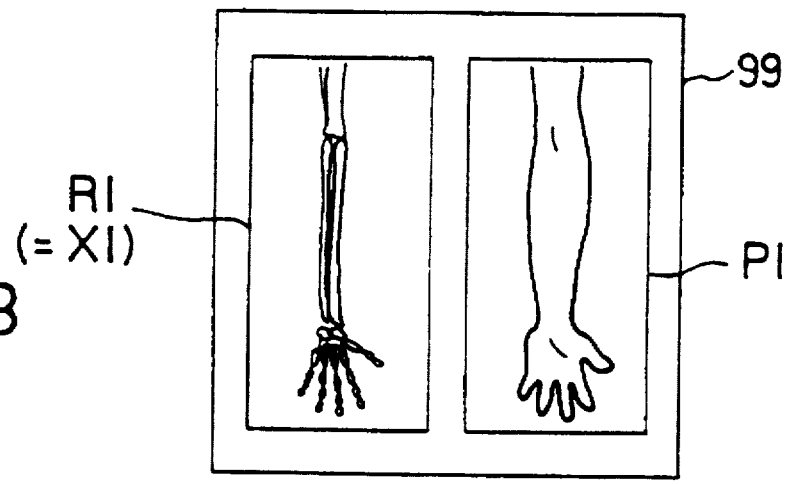
Figure 17C:
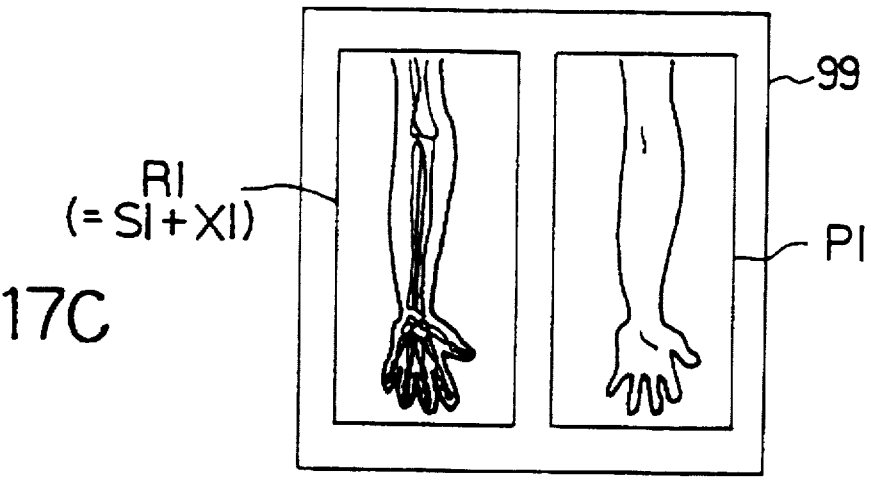

There are three superposing modes in this embodiment, as shown in FIGS. 17A to 17C. The first selection mode is to use only surface image data from the second frame memory 94 (in this case, X-ray image data are not used), thus a superposed reference image RI is made up of only a surface image SI, like shown in FIG. 17A. The second selection mode adopts only X-ray image data from the first frame memory 93 (in this case, surface image data are not concerned), thus a superposed reference image RI is equal to an X-ray image XI, shown in FIG. 17B. The third selection mode is shown in FIG. 17C, in which surface image data and X-ray image data are superposed, thereby a superposed X-ray image XI on a surface image SI being formed as a reference image RI.

The image data RI* of a reference image RI thus-superposed are sent to the image data composing unit 96, to which surface image data SI* are also sent from the TV camera 17 disposed in the liming device 13. The surface image data SI* are specially designated as "positioning image data PI*", when sent to the image data composing unit 96. The composing unit 96 composes image data of each frame by combining a reference image data RI* and a positioning image data PI* in a divided form on a frame memory and send them to a TV monitor 99 for display.

The operation of the present embodiment will be followed. Assume that a surface image and an X-ray image of an arm to be examined had been taken before medical treatment and their image data had been stored in the first and second frame memories 93 and 94. Therefore, after the medical treatment, it is desired to X-ray examine in the same attitude of the arm on the tabletop 12 as one taken before the treatment. In such a case, this X-ray diagnostic apparatus is mostly suitable.

Placing the same diagnostic portion, i.e. the arm, in this case, under the X-ray tube 11, permits the TV camera 17 to take a surface image of the arm in real time and send its data S1* to the TV monitor 23 and the positioning portion 92.

Under such condition, an operator selects, through the input device 98, a mode of a reference image RI for the arm already taken. If the first mode is selected, data of the past surface image of the arm are formed and combined with data of the present surface image, i.e., the positioning image to which positioning will be given into one frame data, through the work of the image data superposing unit 95 and image data composing unit 96.

Accordingly, the composed image data are displayed such as in FIG. 17A, in which the reference image RI consisting of the surface image SI taken before medical treatment is positioned at the left side and the positioning image PI now taken for medical treatment is positioned at the right side.

Then, the operator moves the X-ray tube 11 and/or the tabletop 12 so that both the images RI and PI coincide with each other in terms of positions on the displayed images. Completing this positioning will enable X-ray examination following the positioning to obtain almost the same positional X-ray image as the reference image RI used in positioning. Therefore, positioning is quick for obtaining the same positional X-ray image referred. In particular, the apparatus is preferably used in such a case that the same diagnostic portion is plurally examined over times elapsed.

If the second mode is selected, the monitor 99 display images of a divided form shown in FIG. 17B, in which the left is a reference image RI consisting of the X-ray image XI taken before and the right is a positioning image PI now taken. Further, the third mode is selected, the left is a reference image RI of the superimposed surface image SI and X-ray image XI and the left is a real-time positioning image PI. An operator can select the mode of a reference image RI according to required accuracy of positioning, for example.

Although the above embodiment uses one TV monitor for displaying a reference image and positioning image in a divided form, two separate TV monitors can be used for displaying those images individually. On the other hand, it is possible to use one display monitor in common for both the TV monitor 23 for limiting aperture adjustment and the TV monitor 99 for positioning.

Figure 19A:
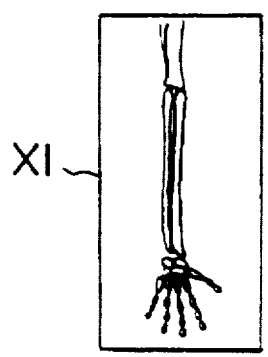
FIGS. 19A to 19C are images explaining superposition of a mark.
Figure 19B:
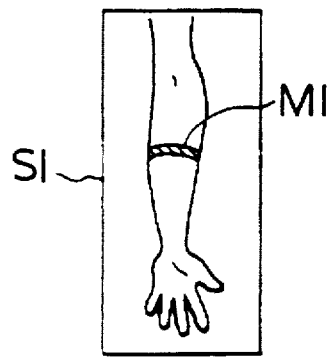
Figure 19C:
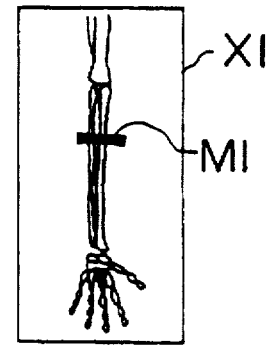
Figure 20:
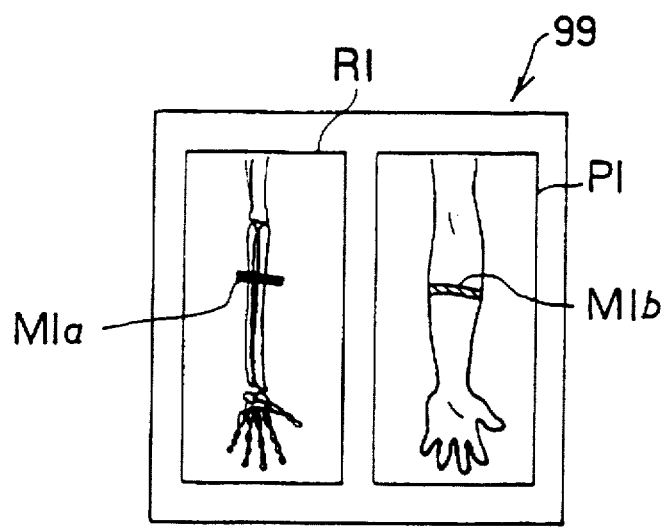
FIG. 20 is an example of a monitor screen displayed in the eighth embodiment.

An eighth embodiment of the present invention will now be explained in accordance with FIGS. 18 to 20.

The above seventh embodiment have been described a positioning technique by which the X-ray tube and/or tabletop are moved, with the TV monitor observed, so that a determined portion (e.e., the tip of a finger) of the reference image RI and the positioning image PI coincides with each other in horizontal and vertical positions on the monitor screen. However, when an X-ray image XI is selected as a reference image RI, positioning might be sometimes hard, because a determined portion such as a finger tip cannot be easily recognized.

The present eighth embodiment will overcome such a difficulty by using a marker attached at a determined position of a patient.

In this embodiment, a marker, through which X-rays are transmitted, is attached at a desired position of a diagnostic portion. The marker is made of a tape or a sign inked and any color is available to the marker.

Figure 18:
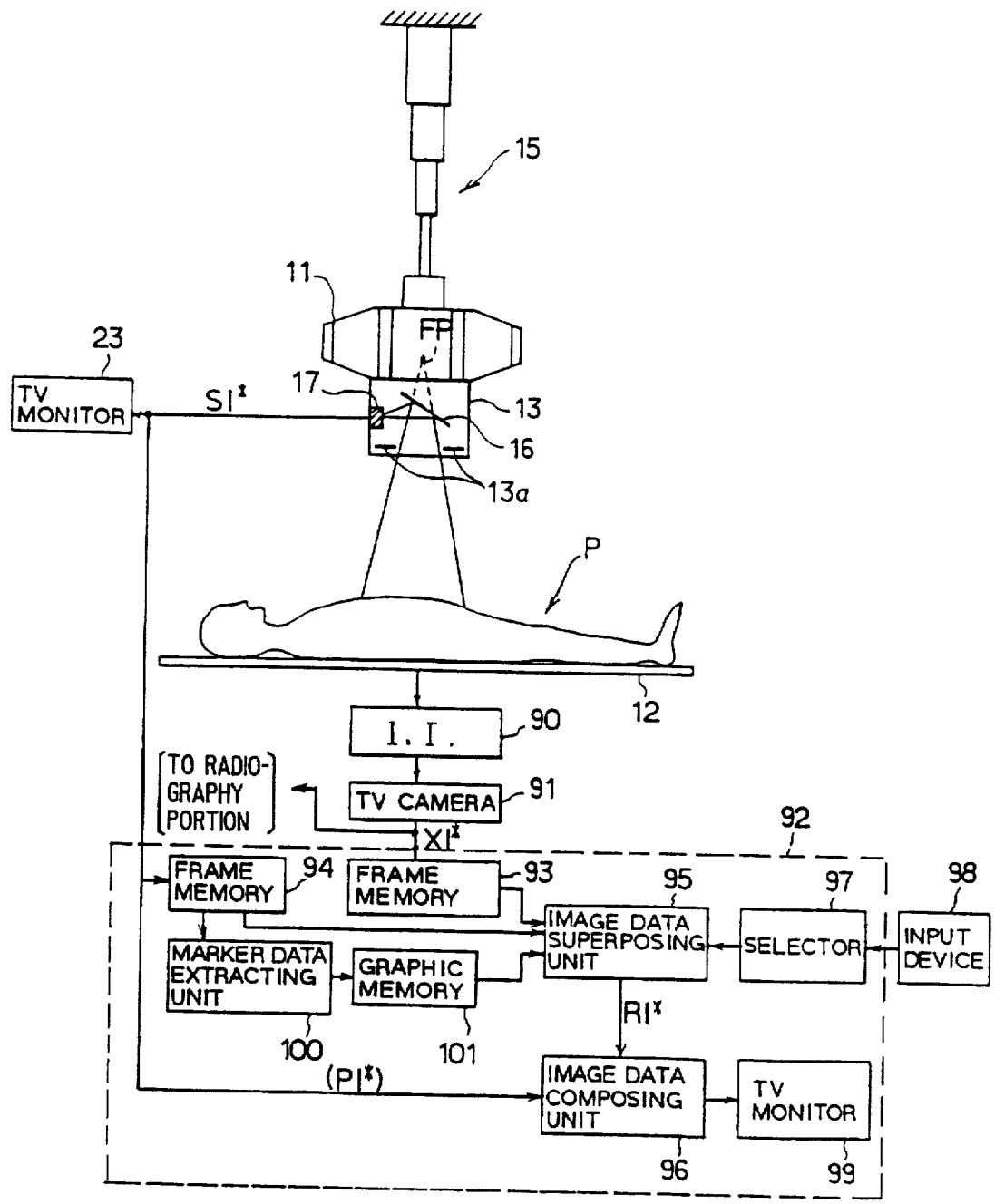
FIG. 18 is a block diagram of an X-ray radiographic apparatus of an eighth embodiment according to the present invention.

The positioning portion 92 shown in FIG. 18 further comprises a marker data extracting unit 100 and a graphic memory 101, in addition to the components of FIG. 16. The marker data extracting unit 100 extracts marker data included in data of a surface image read out from the second frame memory 94 connecting to the TV camera 17. This extraction is carried out by, for instance, distinguishing levels of image data pixel by pixel by a threshold value or distinguishing degrees of brightness of image data pixel by pixel by a threshold value corresponding to the color of a marker, if the marker is colored.

The marker data thus-extracted is then sent to the graphic memory 101, where corresponding graphic data of the marker are formed and sent to the image data superposing unit 95. Thus, when the second display mode of the reference image RI is selected, the superposing unit 95 is to superpose the graphic data of the marker on the X-ray image data read-out from the first frame memory 93. The superposed image data RI* are sent to the image data composing unit 96 to be combine with a positioning image data PI*.

In this embodiment, before medical care for an arm being examined, for example, attached on its desired position is a marker being capable of transmitting X-rays. In this situation, an X-ray image XI (refer to FIG. 19A) is radiographed and its data are stored in the first frame memory 93, whereas a surface image SI (refer to FIG. 19B) is taken with a marker image MI and its image data are stored in the second frame memory 94.

On positioning at the beginning of X-ray examination after the medical care, the marker is again attached on the same place of the arm. When the second display mode is selected, data of the maker image MI already taken are extracted by the marker data extracting unit 100 and its graphic data are sent from the superposing unit 95, in which the data of the marker are superposed on the data of an X-ray image XI taken before the medical care, as shown in FIG. 19C. Since, the image data composing unit 96 receives in real time data of a positioning image PI that compose one frame data with the superposed data of a reference image RI. Therefore, displayed on the monitor 99 is like an image shown in FIG. 20; the left side is the reference image RI having the marker image Mla attached before and the right side is the positioning image PI with the marker image Mlb now attached.

Then, the operator will carry out positioning by moving the X-ray tube 11 and/or the tabletop 12 so that the displayed positions of both the marker Mla and Mlb Coincide with each other. This positioning is remarkably easier than that in the previous embodiment, because the landmarks are put on both the images RI and PI.

The above embodiment can adopt any shape of a marker such as a square, triangle, or even a cross. Moreover, the attachment technique of a marker thus-described can also applied to the above first and third display modes of the reference image.

Furthermore, a ninth embodiment of the present invention will now be described according to FIGS. 21 to 23A and 23B.

This embodiment takes it into account the direction of a reference image displayed together with a positioning image, when an X-ray tube is rotated to radiate X-ray beams in another direction.

Figure 21:
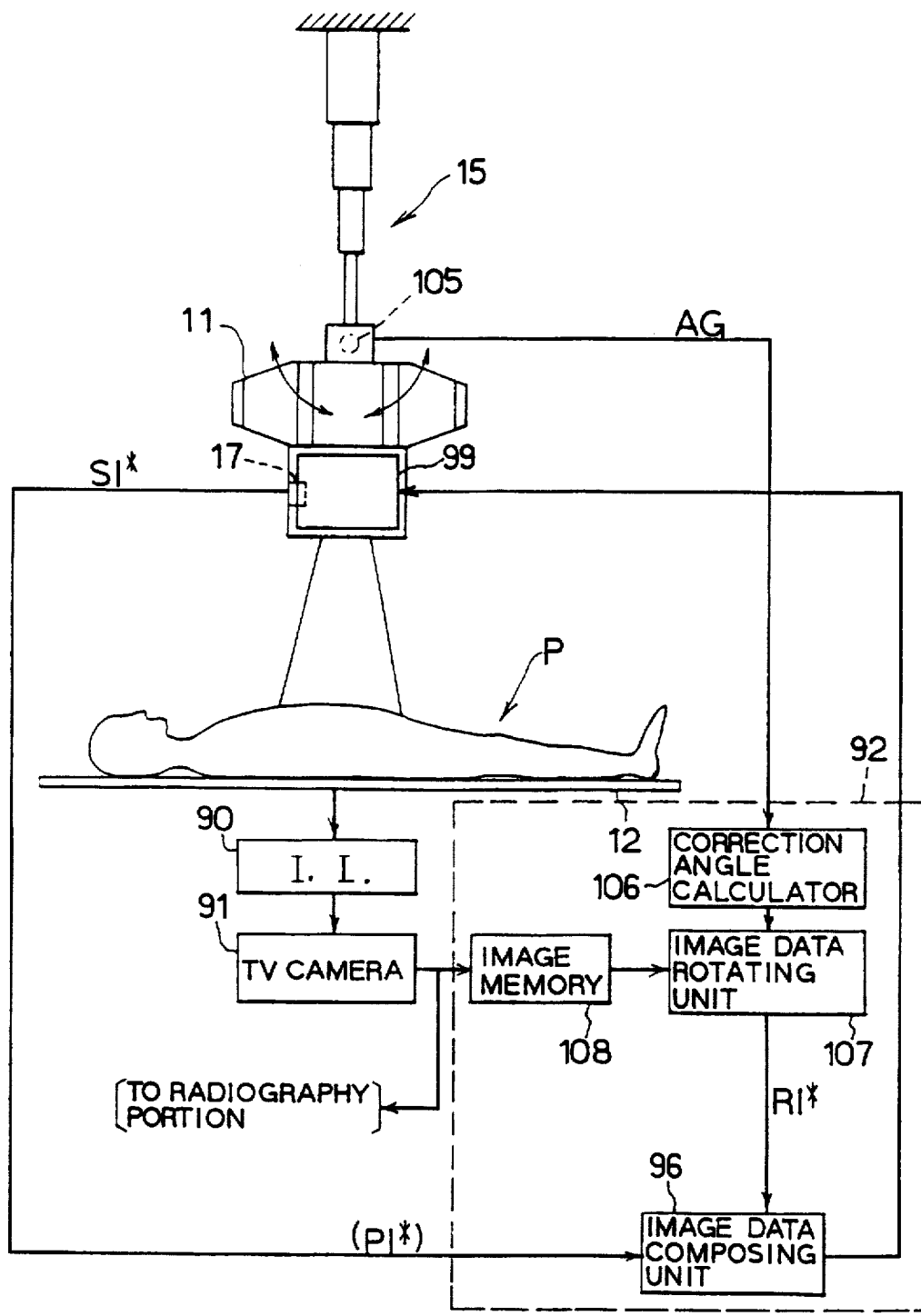
FIG. 21 is a block diagram of an X-ray radiographic apparatus of a ninth embodiment according to the present invention.

In an X-ray radiographic apparatus shown in FIG. 21, the X-ray tube 11 is rotatable by the support device 15, as represented by arrows therein, through a range of 180 degrees, whose center is a downward position, along a plane parallel to the longitudinal axis of the tabletop 12. The rotation angle of the X-ray tube 11 is detected by an angle sensor 105 arranged in the support device 15. The angle sensor 105 is, for example, a touch switch that is capable of detecting three ways; a downward position P1, a horizontal rightward position P2, and a horizontal leftward position P3, as shown in FIG. 22.

The positioning portion 92 has a correction angle calculator 106, which receives an angle signal AG from the angle sensor 105, calculates a necessary correction rotation angle for a reference image which might be different in display direction to a positioning image. This rotation is required when a reference image RI, which have already been taken at the horizontal rightward position P2 in FIG. 22, is used this time for X-ray radiography carried out at the downward position P1 in FIG. 22. Thus, the correction angle calculator 106 have stored, for reference, a rotation angle at the time of X-radiography when the reference image have been taken.

The correction rotation angle thus-calculated is sent to an image data rotating unit 107, to which data of an X-ray image for positioning (the second display mode of the reference image is used, in this embodiment) are also sent via an image memory 108. The image data rotating unit 107 has a memory and rotate the X-ray image data by rewrighting their image data on the inner memory, according to the correction rotation angle supplied. The rotated image data are supplied, as reference image data RI*, to the image data composing unit 96 above-described, to which positioning image data PI* are also sent from the TV camera 17.

Therefore, in the same way as the above-described embodiments, the reference image data RI* and positioning image data PI* are combined into one frame image and sent to the TV monitor 99 which is mounted in the X-ray tube 11. Accordingly, if two radiography positions are different between the two times of radiography in conjunction with positioning, it is possible to avoid such a case shown in FIG.

23A; that is, the display directions between the reference image RI and positioning image PI are opposite to each other. In other words, it is possible to make both the images RI and PI align in the same direction on the TV monitor 99. This correction of a rotation angle enables an operator to facilitate positioning operation remarkably.

The above embodiment can also be applied to the first and third display modes of the reference image described before.

A tenth embodiment of the present invention will now be explained with reference FIGS. 24 to 27.

This embodiment relates to automatic exposure control by means of utilizing data of a surface image taken by a TV camera in an X-ray beam limiting device.

Figure 24:
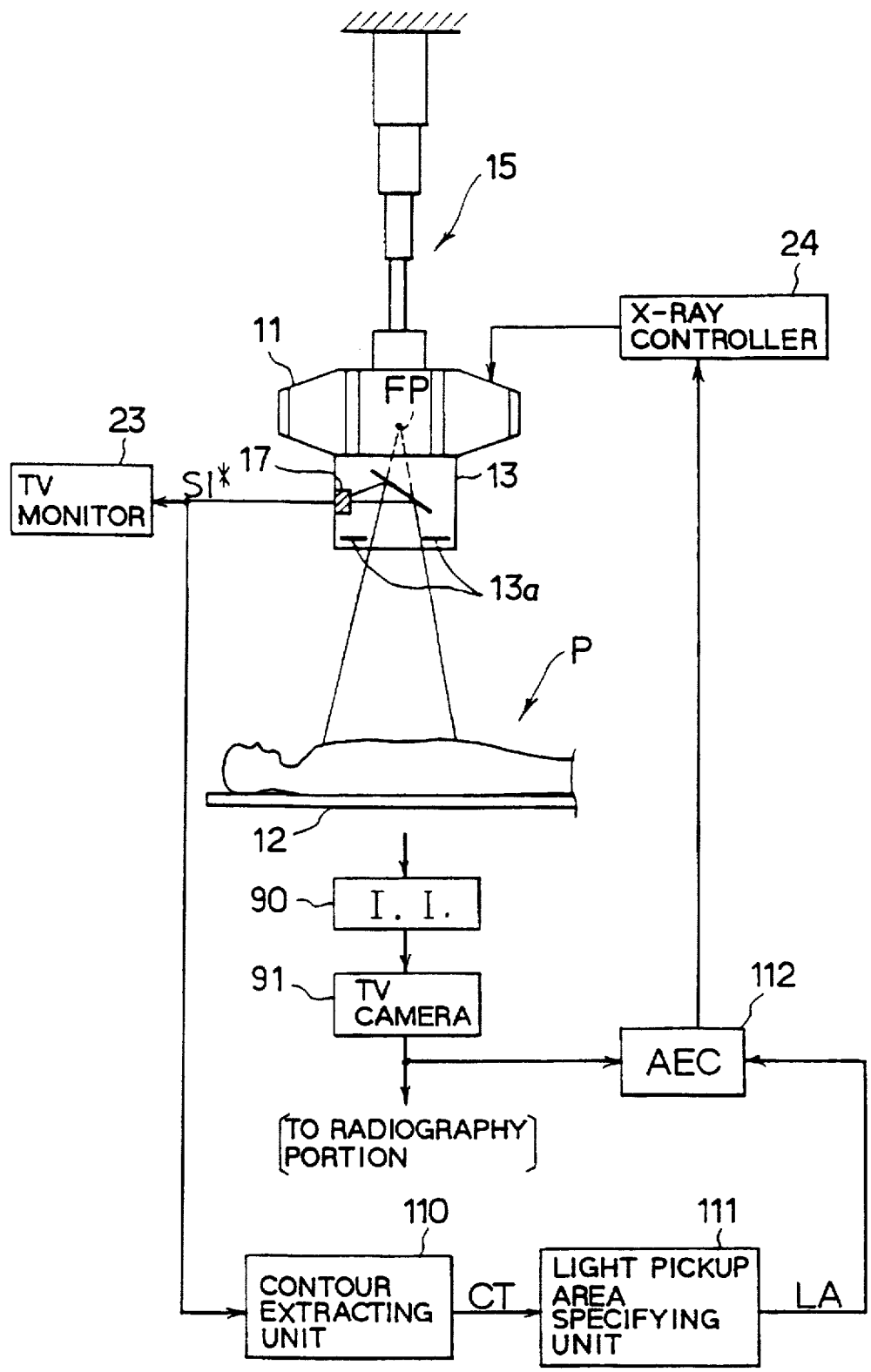
FIG. 24 is a block diagram of an X-ray radiographic apparatus of a tenth embodiment according to the present invention.

An X-ray radiographic apparatus shown in FIG. 24 has a contour extracting unit 110 and a light area pickup specifying unit 111 at the output side of the TV camera 17 in the X-ray beam limiting device 13. Hence, data of a surface image SI* are to be sent to the contour extracting unit 110 that extracts the contour of a patient from the surface image data SI*. In detail, the extraction is carried out by, first, a process of applying spatial filters (differential filters) to the surface data and then, a process of forming binary data which produces such a contour CT as shown in FIG. 25(a). After this, the region within the contour data thus-formed is painted pixel by pixel, thereby producing an image on an inner memory, as shown in FIG. 25(b), for instance.

Instead of the above contour extraction technique, another one can also be adopted that distinguishes the color(e.g., red, blue, or green) of a tabletop 12 from the color of a patient and recognizes a difference in color as a contour by applying a threshold level to their color data.

The data of a contour thus-extracted and formed are supplied to the light pickup area specifying unit 111, which specifies a light pickup area, according to a predetermined procedure and the contour data. For instance, the specifying process is as follows. First, an initial light pickup area LAi having a predetermined shape, such as an approximate circle, is placed automatically in a predetermined area, such as a central part of a frame data (refer to FIG. 26(b)). Next, a common light pickup area LAc is extracted between the initial light pickup area LAi and the painted contour image CT by means of AND operation pixel by pixel, as shown in FIG. 26(b). This extraction causes some of the pixels within the initial light pickup area LAi to drop off, which are exemplified by dotted lines in FIG. 26(b). Finally, the remaining pixels, as shown in FIG. 26(c), form a specified light pickup area LA for controlling X-ray exposure.

Data of a light pickup area LA thus-specified are sent to an automatic exposure controller (AEC) 112, to which data of an X-ray image for radiography are sent. The automatic exposure controller 112 counts a total X-ray amount falling on the total number of pixels of the supplied light pickup area LA and then control the X-ray controller 24 by stopping it when the total X-ray integral amount on all the pixels of the light pickup area LA reaches a determined threshold value.

The light pickup area can be formed in any shape and size, such as a square as shown in FIG. 27, where two square light pickup areas LA and LA are specified on X-ray images of both the legs for exposure control.

In this way, the surface image taken by the TV camera is used for automatic exposure control through processing of contour extraction and light pickup area specification. Accordingly, required operation for an operator is only placing a patient such that a patient's portion to be radiographed appears on a TV screen. This enables the automatic specification of a light pickup area at a proper position, eliminating specification of it by hand and reducing operation work, besides appropriate exposure control.

The above embodiments uses an ordinary optical TV camera as a surface image obtaining means, but the present invention is not limited to it, an infrared camera is usable, for instance.

For the sake of completeness it should be mentioned that the embodiment examples shown in the figures are not a definitive list of possible embodiments. The expert will appreciate that it is possible to combine the various construction details or to supplement or modify them by measures known from the prior art without departing from the basic inventive principle.

What we claim is:

1. An X-ray radiographic apparatus for radiographing an X-ray image of an object, comprising:

an X-ray tube having an X-ray focal point for radiating X-ray beams toward the object;

an X-ray beam limiting device incorporating a limiting member making an adjustable aperture in size limiting the X-ray beams passing therethrough, the limiting member being positioned between the X-ray tube and the object;

means for obtaining a surface image of the object viewing through the aperture, the surface image obtaining means having an optical mirror passing the X-ray beams and being arranged between the X-ray tube and the limiting member on the way of an X-ray beam path formed by the X-ray beams, and an optical imaging element producing the surface image responsively to light rays received through the aperture by optical reflection at the mirror;

means for forming a frame image representing a target size of the aperture in accordance with a given size information; and means for displaying the surface image on which the frame image is superposed.

2. An X-ray radiographic aperture according to claim 1, further comprising:

a specifying means for specifying a desired size of the frame image by giving the size information to the frame image forming means.

3. An X-ray radiographic apparatus according to claim 2, further comprising:

means for driving the limiting member so as to control an actual size of the aperture into a predetermined full open until the target size of the aperture is determined.

4. An X-ray radiographic apparatus according to claim 3, further comprising:

another means for driving the limiting member so as to control the actual size of the aperture into the desired size of the frame image specified by being determinedly displayed on the surface image displaying means after the target size of the aperture is determined.

5. An X-ray radiographic apparatus according to claim 1, wherein the optical imaging element is an optical camera means for photographing the surface image, the camera means being incorporated in the X-ray beam limiting device.

6. An X-ray radiographic apparatus according to claim 5, wherein the optical mirror is disposed so as to reflect the light rays received through the aperture from the object into a side direction to the X-ray beam path and make the light rays converge at an optically conjugate position to a position of the X-ray focal point, the optically conjugate position lying within the X-ray beam limiting device.

7. An X-ray radiographic apparatus according to claim 6, wherein the camera means is disposed at the optically conjugate position.

8. An X-ray radiographic apparatus according to claim 7, wherein the camera means is an infrared TV camera.

9. An X-ray radiographic apparatus according to claim 4, wherein the X-ray focal point is one in number.

10. An X-ray radiographic apparatus according to claim 4, wherein the surface image displaying means comprises a monitor having a screen for displaying the surface image superposed by the frame image and the frame image specifying means has a touch panel attached on a front surface of the screen of the monitor, the touch panel being used by hand for producing the size information in accordance with a given specification mode of the size information.

11. An X-ray radiographic apparatus according to claim 10, further comprising a selecting means for selecting by hand one of a plurality of specification modes prepared as the specification mode.

12. An X-ray radiographic apparatus according to claim 11, wherein the frame image is a square frame image and the specification modes include a first mode specifying separately positions of four segments of the square frame image, a second mode specifying positions of two adjacent segment of the square frame image, and a third mode specifying a position of one corner point of the square frame image.

13. An X-ray radiographic apparatus according to claim 7, wherein the camera means is a TV camera.

14. An X-ray radiographic apparatus for radiographing an X-ray image of an object, comprising:

an X-ray tube having two X-ray focal points for each radiating X-ray beams toward the object;

an X-ray beam limiting device incorporating two limiting members each making an adjustable aperture in size for limiting the X-ray beams passing therethrough, each of the two limiting members being positioned between the X-ray tube and the object;

means for obtaining two surface images of the object viewing through each of the two apertures, the surface image obtaining means having two optical mirrors passing the X-ray beams and each being arranged between the X-ray tube and each of the two limiting members on the way of an X-ray beam path formed by each of the two X-ray beams, and an optical imaging element producing the two surface images responsively to light rays of the object received through each of the two apertures by optical reflection at each of the two mirrors; and means for displaying the surface images.

15. An X-ray radiographic apparatus according to claim 13, wherein the optical imaging element consists of two optical camera means for each photographing the surface image, the camera means being incorporated in the X-ray beam limiting device.

16. An X-ray radiographic apparatus according to claim 15, wherein each of the two optical mirrors is disposed so as to reflect the light rays received through the aperture from the object into a side direction to the X-ray beam path and make the light rays converge at an optically conjugate position to a position of the X-ray focal point, the optically conjugate position lying within the X-ray beam limiting device.

17. An X-ray radiographic apparatus according to claim 16, wherein the two camera means are each disposed at the two optically conjugate positions.

18. An X-ray radiographic apparatus according to claim 17, wherein the surface image displaying means comprises two monitors for each displaying the surface images obtained by each of the two camera means.

19. An X-ray radiographic apparatus according to claim 17, wherein the surface image displaying means comprises one monitor for displaying the two surface images obtained by the two camera means and a switch means for selectively exchanging signals of the two surface images supplied from the two camera means to the one monitor.

20. An X-ray radiographic apparatus according to claim 14, wherein the optical imaging element consists of one optical camera means for photographing the two surface images, the camera means being incorporated in the X-ray beam limiting device and being an optical camera disposed at an optically conjugate position to positions of the two X-ray focal points, and the apparatus further comprises means for selectively exchanging to the optical camera two optical paths traveling from the object to the optical camera through the two apertures.

21. An X-ray radiographic apparatus according to claim 20, wherein the optical path exchanging means comprises two optical systems for guiding the reflected light-rays from the object to the camera along the two optical paths, two shutter means for optically opening and closing the two optical paths, and a control means for selectively driving the two shutter means into states of opening and closing of the two shutter means.

22. An X-ray radiographic apparatus according to claim 21, wherein each of the two shutter means is a shutter formed by a liquid crystal.

23. An X-ray radiographic apparatus according to claim 22, wherein the surface image displaying means has one monitor alternately displaying the two surface images.

24. An X-ray radiographic apparatus according to claim 22, wherein the surface image displaying means has one monitor for displaying the two surface images and the apparatus further comprises means for supplying R(right) and L(left) images, corresponding to the two X-ray focal points, to the monitor.

25. An X-ray radiographic apparatus according to claim 24, wherein the image supplying means includes a memory means for storing data of the R- and L-images, the memory means having a memory of a double buffer structure.

26. An X-ray radiographic apparatus according to claim 22, wherein the surface image displaying means has two monitors for displaying the two surface images and the apparatus further comprises means for distributing R(right) and L(left)images corresponding to the two X-ray focal points, to the two monitors.

27. An X-ray radiographic apparatus according to claim 26, wherein the image distributing means includes a memory means for storing data of the R- and L-images, the memory means having a memory of a double buffer structure.

28. An X-ray radiographic apparatus comprising:

an X-ray tube having an X-ray focal point for radiating X-ray beams toward an object being examined;

an X-ray beam limiting device incorporating a limiting member making an aperture for limiting the X-ray beams passing therethrough, the limiting member being positioned between the X-ray tube and the object;

means for radiographing an X-ray image based on the X-ray beams transmitted through the object;

means for obtaining a surface image of the object viewing through the aperture, the surface image obtaining means having an optical mirror passing the X-ray beams and being arranged between the X-ray tube and the limiting member on the way of an X-ray beam path formed by the X-ray beams, and an optical imaging element producing the surface image responsively to light rays received through the aperture by optical reflection at the mirror;

means for obtaining a reference image of the object for positioning to the object, the reference image being made from image data of the same object acquired in the past; and means for combinedly displaying the surface image currently obtained and the reference image obtained in the past.

29. An X-ray radiographic apparatus according to claim 28, wherein the optical imaging element is an optical camera means for photographing the surface image, the camera means being incorporated in the X-ray beam limiting device.

30. An X-ray radiographic apparatus according to claim 29, wherein the optical mirror is disposed so as to reflect the light rays received through the aperture from the object into a side direction to the X-ray beam path and make the light rays converge at an optically conjugate position to a position of the X-ray focal point, the optically conjugate position lying within the X-ray beam limiting device.

31. An X-ray radiographic apparatus according to claim 30, wherein the camera means is disposed at the optically conjugate position.

32. An X-ray radiographic apparatus according to claim 28, wherein the camera means is a TV camera.

33. An X-ray radiographic apparatus according to claim 28, wherein the reference image obtaining means includes at least one of two memory means each storing x-ray image data acquired in the past by the X-ray image radiographing means and storing surface image data acquired in the past by the surface image obtaining means, and means for forming the reference image on the basis of at least one of the past X-ray radiographic image data and the past surface image data.

34. An X-ray radiographic apparatus according to claim 28, wherein the displaying means is a means that displays a divided image of the past reference image and the current surface image.

35. An X-ray radiographic apparatus according to claim 28, further comprising means for extracting data of a marker image from data of the surface image obtained by the surface image obtaining means on condition that a marker means transmitting the X-ray beams therethrough is set on a diagnostic portion of the object, thereby the data of surface image containing data of the mark image, and means for forming the reference image by superposing the data of the marker image on the data of the X-ray image.

36. An X-ray radiographic apparatus according to claim 35, wherein the marker means is a color tape.

37. An X-ray radiographic apparatus according to claim 28, further comprising:

means for detecting a rotation angle of the X-ray tube when the X-ray tube is rotated for radiography;

means for calculating a correction angle to make a direction of the reference image coincide with a direction of the surface image obtained from the surface image obtaining means; and means for rotating the reference image on the basis the calculated correction angle.

38. An X-ray radiographic apparatus according to claim 37, wherein the X-ray tube is rotatable in a plane containing three ways in regard to a fixed point of the X-ray tube, the three ways being a downward position and right- and leftward side positions.

39. An X-ray radiographic apparatus according to claim 33, wherein the X-ray image radiographic means has an image intensifier receiving the X-ray beams transmitted through the object.

40. An X-ray radiographic apparatus according to claim 35, further comprising means for specifying one display mode of the reference image from a plurality of display modes prepared.

41. An X-ray radiographic apparatus according to claim 40, wherein the plurality of display modes are at least two of a first display mode specifying only a past X-ray image, a second display mode specifying only the past surface image, and a third display mode specifying a superposed image of the past X-ray image and the past surface image.

42. An X-ray radiographic apparatus for radiographing an X-ray image of an object, comprising:

an X-ray tube having an X-ray focal point for radiating X-ray beams toward the object;

an X-ray beam limiting device incorporating a limiting member making an aperture for limiting the X-ray beams passing therethrough;

means having a receiving element for receiving the X-ray beams pixel by pixel transmitted through the object;

means for obtaining a surface image of the object viewing through the aperture;

means for extracting a contour image of the object from the surface image;

means for setting a light pickup area on the extracted contour image, the light pickup area being changeable in size and location in accordance with a size and location of the contour image; and means for controlling an X-ray beam output of the X-ray tube on the basis of an amount of the X-ray beams received through the light pickup area assigned on the receiving element.

43. An X-ray radiographic apparatus according to claim 42, wherein the light pickup area setting means is a means designating a common pixel area forming the light pickup area of the contour image and a predetermined initial light pickup area image automatically set.

44. An X-ray radiographic apparatus according to claim 43, wherein the X-ray exposure controlling means is a means for controlling the X-ray beam output of the X-ray tube on the basis of an integral X-ray amount received through the light pickup area assigned on the receiving element.

45. An X-ray radiographic apparatus according to claim 42, wherein the surface image obtaining means comprises an optical camera means for photographing the surface image, the camera means being incorporated in the X-ray beam limiting device.

46. An X-ray radiographic apparatus according to claim 45, wherein an optical mirror is disposed so as to reflect the light rays received through the aperture from the object into a side direction to the X-ray beam path and make the light rays converge at an optically conjugate position to a position of the X-ray focal point, the optically conjugate position lying within the X-ray beam limiting device.

47. An X-ray radiographic apparatus according to claim 46, wherein the camera means is disposed at the optically conjugate position.

48. An X-ray radiographic apparatus according to claim 47, wherein the camera means is a TV camera.

49. An X-ray radiographic apparatus according to claim 42, wherein the limiting member is placed between the X-ray tube and the object and the surface image obtaining means has an optical mirror passing the X-ray beams and being arranged between the X-ray tube and the limiting member on the way of an X-ray beam path formed by the X-ray beams, and an optical imaging element producing the surface image responsively to light rays received through the aperture by optical reflection at the mirror.

* * * * *